United States Patent
Ise et al.

(10) Patent No.: US 6,794,155 B2
(45) Date of Patent: Sep. 21, 2004

(54) *TREPONEMA PALLIDUM* FUSED ANTIGEN AND ASSAY FOR ANTI-TREPONEMA PALLIDUM ANTIBODIES USING THE SAME FUSED ANTIGEN

(75) Inventors: Nobuyuki Ise, Mitaka (JP); Takeya Hori, Hachioji (JP); Katsuya Fujimura, Iruma (JP); Tetsuji Tanimoto, Tokyo (JP); Masahisa Okada, Hachioji (JP)

(73) Assignee: Fujirebio Inc., Tokyo (JP)

( * ) Notice: Subject to any disclaimer, the term of this patent is extended or adjusted under 35 U.S.C. 154(b) by 640 days.

(21) Appl. No.: 09/761,667

(22) Filed: Jan. 18, 2001

(65) Prior Publication Data

US 2001/0002311 A1 May 31, 2001

Related U.S. Application Data

(62) Division of application No. 08/773,106, filed on Dec. 26, 1996, now Pat. No. 6,248,331.

(30) Foreign Application Priority Data

Dec. 25, 1995 (JP) .............................................. 7-350072

(51) Int. Cl.$^7$ ............................................... G01N 33/53
(52) U.S. Cl. ........................... 435/7.9; 435/7.1; 436/518
(58) Field of Search ......................... 435/7.9, 7.1, 7.92, 435/7.93, 7.94, 7.95, 7.2, 7.22, 7.36; 436/518

(56) References Cited

U.S. PATENT DOCUMENTS 4,976,958 A * 12/1990 Shinnick et al.

FOREIGN PATENT DOCUMENTS

| EP | 0670494 | * | 9/1995 |
| WO | 95/04145 | * | 2/1995 |
| WO | 95/12676 | * | 5/1995 |

OTHER PUBLICATIONS

Weigel et al (Infection and Immunity, 60(4):1568–76, 4/92).*

* cited by examiner

*Primary Examiner*—Patricia A. Duffy
(74) *Attorney, Agent, or Firm*—Oblon, Spivak, McClelland, Maier & Neustadt, P.C.

(57) ABSTRACT

A *Treponema pallidum* fused antigen in which at least two surface antigens of *Treponema pallidum* are fused and an assay for anti-*Treponema pallidum* antibodies, using the above *Treponema pallidum* fused antigen.

14 Claims, 11 Drawing Sheets

DETAILED DIAGRAM OF EXPRESSION VECTOR pW6A

| | |
|---|---|
| T7$^p$ | : T7 PROMOTER |
| lac$^o$ | : lac OPERATER |
| SD | : SHINE-DALGARNO SEQUENCE |
| TT | : T7 TRANSCRIPTIONAL TERMINATOR |
| Amp r | : β LACTAMASE |
| lacI$^q$ | : lac REPRESSOR |
| pBR322 ori | : REPLICATION ORIGIN |

PREPARATION OF GENE ENCODING 47K ANTIGEN

PREPARATION OF GENE ENCODING
15K ANTIGEN AND 17K ANTIGEN

FIG. 5
DETAILED DIAGRAM OF EXPRESSION VECTOR FOR THREE-ANTIGEN FUSED ANTIGEN
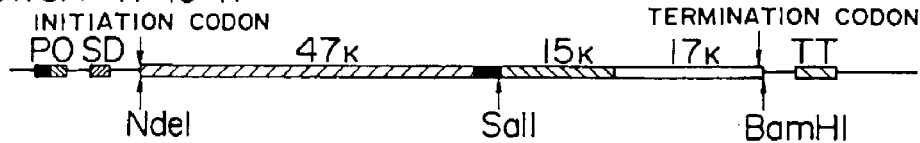
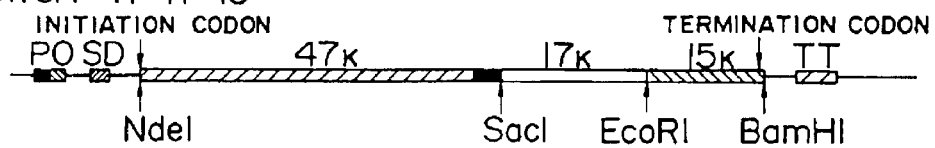
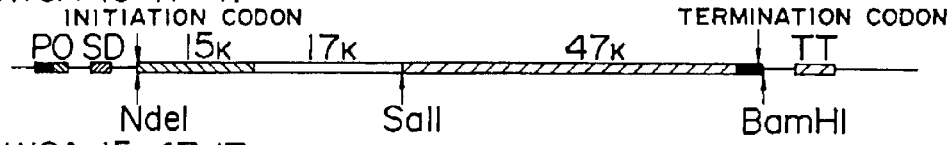
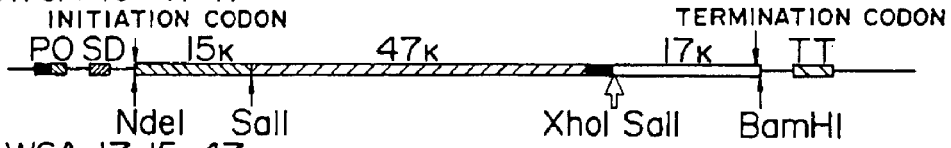
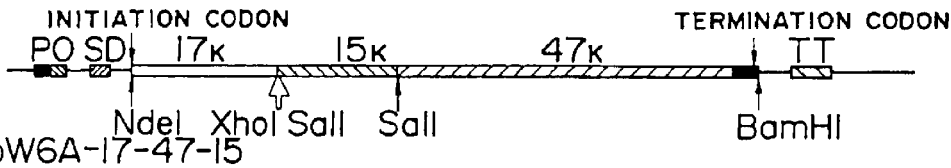
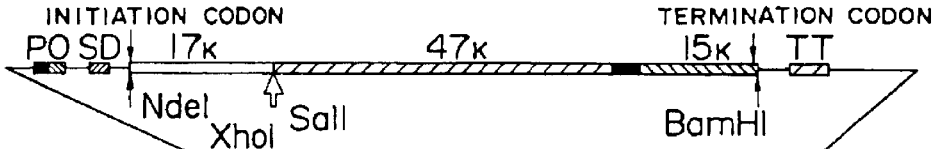
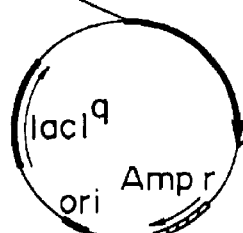

FIG. 6
pW6A-15
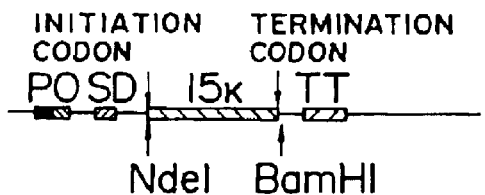
pW6A-15-15
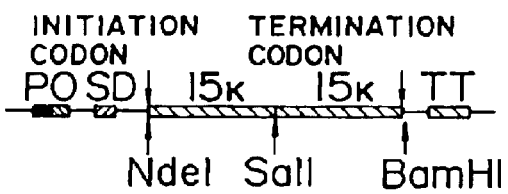
pW6A-15-15-15
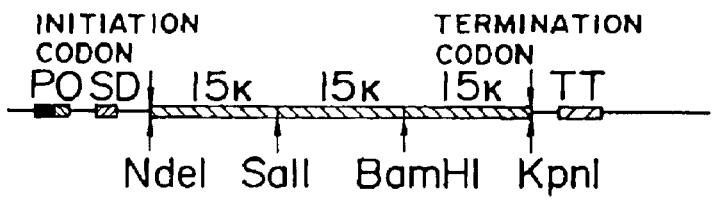
pW6A-15-15-15-15
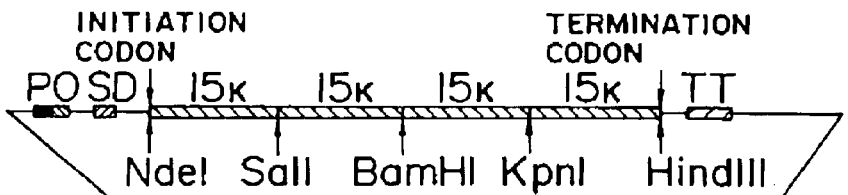
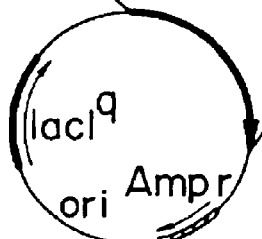

TREPONEMA PALLIDUM FUSED ANTIGEN AND ASSAY FOR ANTI-TREPONEMA PALLIDUM ANTIBODIES USING THE SAME FUSED ANTIGEN

This application is a divisional of U.S. application Ser. No. 08/773,106, filed on Dec. 26, 1996, now U.S. Pat. No. 6,248,331.

BACKGROUND OF THE INVENTION

1. Field of the Invention

The present invention relates to *Treponema pallidum* fused antigen and an assay for anti-*Treponema pallidum* antibodies, using the same fused antigen.

2. Discussion of Background

Syphilis is an infectious disease caused by *Treponema pallidum*. *Treponema pallidum* belongs to the order Spirochaetales. It has been established that several kinds of surface antigens exist on the cell surface as antigens of *Treponema pallidum* (The Journal of Immunology, Vol. 129, p. 833–838, 1982; The Journal of Immunology, Vol. 129, p. 1287–1291, 1982; Journal of Clinical Microbiology, Vol. 21, p. 82–87, 1985; Journal of Clinical Microbiology, Vol. 30, p. 115–122, 1992).

When the body is infected with *Treponema pallidum* (hereinafter referred to as Tp), anti-Tp antibodies are evoked and produced in the blood by those surface antigens, so that the diagnosis of syphilis is made by inspecting the presence or absence of the anti-Tp antibodies in the blood.

Generally immunoassays using the antigen-antibody reaction between the Tp antigens and the anti-Tp antibodies in the blood are utilized in order to detect the presence or absence of the anti-Tp antibodies in the blood of the patient.

For conducting the immunoassay for the Tp antibodies, a large amount of the Tp antigens is required. However, a large amount of Tp cannot be cultivated in vitro, so that conventionally Tp is inoculated into the testes of the rabbit and the Tp antigen is obtained from the testes of the rabbit infected with Tp and purified for use (Acta Pathol Microbiol Scand [B], Vol. 83, p. 157–160, 1975).

The above-mentioned rabbit testicular inoculation method, however, has the problems that the Tp antigen is contaminated with impurities since Tp is cultivated in vivo in the rabbits, and the cultivated Tp varies due to individual differences of rabbits, and it is extremely difficult to obtain a large amount of Tp antigen with excellent reproducibility.

Recently, because of the development of genetic engineering, the technology of
artificially mass producing the Tp antigens has been developed by cloning a gene which encodes the surface antigen of Tp (Science, Vol. 216; p. 522–523, 1982; Infection and Immunity, Vol. 36, p. 1238–1241, 1982; Infection and Immunity, Vol. 41, p. 709–721, 1983; Infection and Immunity, Vol. 42, p. 435–445, 1983; Infection and Immunity, Vol. 42, p. 187–196, 1983; Journal of Bacteriology, Vol. 162, p. 1227–1237, 1985; Infection and Immunity, Vol. 54, p. 500–506, 1986; Infection and Immunity, Vol. 56, p. 71–78, 1988; Infection and Immunity, Vol. 57, p. 2612–2623, 1989; Infection and Immunity, Vol. 57, p. 3708–3714, 1989; Molecular Microbiology, Vol. 4, p. 1371–1379, 1990; Infection and Immunity, Vol. 58, p. 1697–1704, 1990; Infection and Immunity, Vol. 61, p. 1202–1210, 1993; Laid-Open Patent Application 2-500403).

By using the technology of genetic engineering, the Tp antigen can be mass produced without using living animals. However, with respect to some kinds of Tp surface antigens, almost no product is expressed by using only the gene which encodes the same antigen itself.

Therefore, in the above-mentioned case, a method of expression of the desired antigen has been proposed using a fused gene which is prepared by joining a gene such as thioredoxin derived from *Escherichia coli* (hereinafter referred to as TRX) or a
glutathione S-transferase derived from *Schisstosoma japonicum* (hereinafter referred to as GST) and a gene of the desired material as disclcosed in Japanese Laid-Open Patent Application 5-507209 and Japanese Laid-Open Patent Application 1-503441.

It has been discovered that a GST15 kDa antigen which is a fused gene of GST and a 15 kDa antigen which is one surface antigen of Tp, and a GST17 kDa antigen which is a fused gene of GST and 17 kDa antigen which is another surface antigen of Tp, exhibit high sensitivity when used for the assay of the anti-Tp antibody as disclosed in Japanese Laid-Open Patent Application 7-63365.

Since *Escherichia coli* and *Schisstosoma japonicum* can live in the human body and therefore there are many people who have a factor in the blood which reacts with TRX or GST. In such a case, even if the person is not infected with Tp, a positive reaction is exhibited with respect to infection with Tp. Thus, it is evident that this has a serious effect on the diagnosis of infection with Tp.

At present, syphilis is completely curable because of the development of antibiotics. Therefore, it is desired that syphilis be cured based on a quick and accurate diagnosis of syphilis. In order to achieve this, there is a keen demand for an assay of Tp antigens and anti-Tp antibodies, with high sensitivity and specificity.

SUMMARY OF THE INVENTION

It is therefore a first object of the present invention to provide *Treponema pallidum* (Tp) fused antigens in which at least two surface antigens of *Treponema pallidum* are fused.

A second object of the present invention is to provide an assay method for anti-*Treponema pallidum* antibodies, using the above-mentioned *Treponema pallidum* fused antigen.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5 is a detailed diagram of an expression vector for a three-antigen fused antigen.

FIG. 6 is a detailed diagram of an expression vector for an antigen in which 15K is repeatedly fused.

DESCRIPTION OF THE PREFERRED EMBODIMENTS

Figure 1:
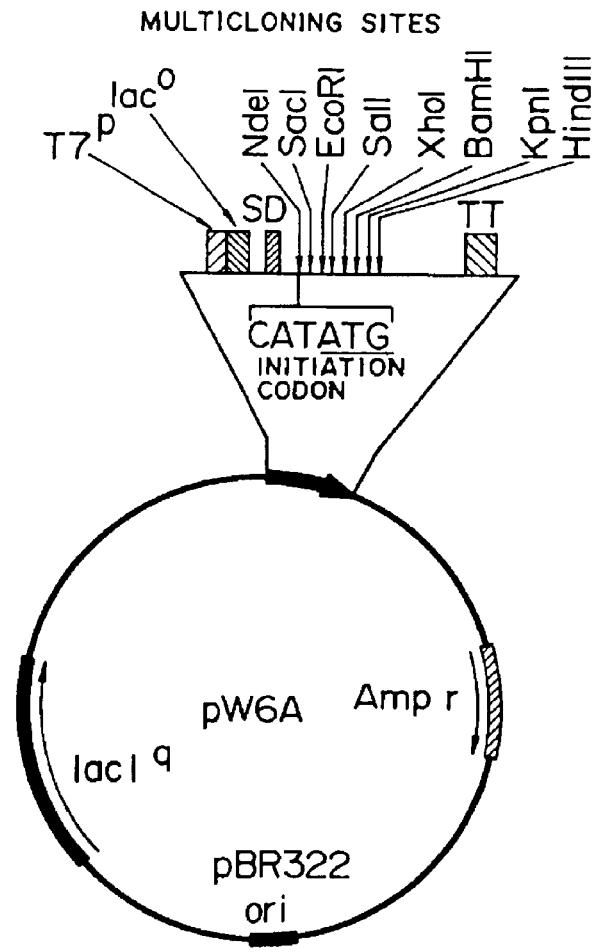
FIG. 1 is a detailed diagram of an expression vector for pW6A.

The inventors of the present invention expressed a Tp fused antigen which is fused with several classes of surface antigens by using a gene which encodes the Tp fused antigen. As a result, it was discovered that expression is significantly increased in comparison with the amount of conventional expression. Furthermore, it was discovered that by using the Tp fused antigen as the antigen for the assay of the anti-Tp antibody, the anti-Tp antibody can be detected with higher sensitivity than that of an assay system using surface antigens individually. The present invention is based on such surprising discoveries.

Surface antigens with various molecular weights are present on the surface of the cells of Tp. As representative surface antigens, antigens with molecular weights of 15 kDa, 17 kDa, 42 kDa and 47 kDa are known (The Journal of Immunology, Vol. 129, p. 833–838, 1982; The Journal of Immunology, Vol. 129, p. 1287–1291, 1982; Journal of Clinical Microbiology, Vol. 21, p. 82–87, 1985; Journal of Clinical Microbiology, Vol. 30, p. 115–122, 1992). These antigens are designated TpN15, TpN17, TpN44.5(a) and TpN47 by S. J. Norris et al. (Microbiological Reviews, Vol. 57, P. 750–779). Hereinafter, a Tp surface antigen with a molecular weight of 47 kDa may be referred to as 47K, a Tp surface antigen with a molecular weight of 17 kDa may be referred to as 17K, and a Tp surface antigen with a molecular weight of 15 kDa may be referred to as 15K.

The genes which encode these surface antigens are already cloned so that such antigens are produced by genetic engineering. Furthermore, the sequences of amino acids of those genes are also determined (Molecular Microbiology, Vol. 4, p. 1371–1379, 1990; Infection and Immunity, Vol. 61, p. 1202–1210, 1993; Infection and Immunity, Vol. 10, p. 1568–1576 1992; Infection and Immunity, Vol. 57, p. 3708–3714, 1989).

The surface antigens of Tp to be used for the fused antigens of the present invention as used hereinafter means all the surface antigens which are present on the surface of the cells of Tp. For example, antigens such as 47K, 17K and 15K are such surface antigens.

Furthermore, the surface antigens for use in the present invention can be appropriately modified to such an extent that the antigenicity thereof is not impaired. For example, there is a signal peptide of about 20 amino acids in the N terminal portion of the Tp surface antigens when those antigens are translated in the cell. However, in a native antigen, such a signal peptide is eliminated. It is considered that this is because the signal peptide is cut by a signal peptidase II after the DNA translation of the surface antigens (Microbial Pathogenesis, Vol. 7, p. 175–188, 1989; Infection and Immunity, Vol. 60, p. 1202–1210, 1993; Molecular Microbiology, Vol. 4, p. 1371–1379, 1990; Infection and Immunity, Vol. 60, p. 1568–1576, 1993).

In the fused antigens of the present invention, the antigens which can be employed include both antigens which contain such signal peptides at the N-terminuses thereof, and antigens which do not contain such signal peptides at the N-terminus thereof.

For example, it is reported that there is a possibility that a further 9 amino acids are joined to the C-terminus of 434 amino acids in 47K (Infection and Immunity, Vol. 60, p1568–1576, 1992). In such a case, PCR is performed using the following primers. The sense primer and anti-sense primer are designed so as not to contain the coding sequence for the signal peptide, but so as to contain the coding sequence for the 9 amino acids joined to the C-terminus, respectively.

The Tp fused antigens of the present invention are antigens that are expressed by fusing the genes of these surface antigens together. When fusing the genes of these Tp surface antigens, any combination of the Tp surface antigens can be employed and there is no restriction to the combination thereof, since either different antigens or the same antigens may be combined.

For expressing the fused antigens of the present invention, conventional genetic engineering technology can be employed. To be more specific, a genomic DNA is extracted from the Tp which is cultivated, for instance, in the testes of rabbits, and used as a template.

PCR is performed to obtain the DNA fragment which encodes each surface antigen. Each fragment is amplified using primers which are prepared based on the known DNA sequence. The resultant DNA fragments are fused by recombinant PCR method (or so-called assemble PCR) or with DNA ligase.

The host such as *Escherichia coli* is transformed using a vector into which this DNA fragment is inserted, and such a bacterium is propagated, for instance, by culturing, whereby the expression of the fused antigen is carried out. Thereafter, a desired fused antigen is obtained through purification such as destruction of the host, or electrophoresis (Molecular Cloning A LABORATORY MANUAL SECOND EDITION 1989).

DNA fragments of the Tp antigen to be fused can be inserted into the vector using restriction endonuclease recognition sites such as Nde I, Sac I, EcoR I, Sal I, Xho I, BamH I, Kpn I, and Hindi III in the multi-cloning site.

The DNA fragment can be inserted into the vector either separately or with such DNA fragments being directly joined in advance, for instance, by recombinant PCR method (or so-called assemble PCR).

When DNA fragments are inserted into the vector using these restriction endonuclease recognition sites, a short amino acid may be caught between the inserted DNA fragments as a linker. This linker can be removed by the following steps. The DNA fragments are fused by recombinant PCR method (or so-called assemble PCR), and the resultant fused DNA fragment is inserted into the multi-cloning sites of the expression vector. Alternatively, the fused antigen may be expressed without removing the linker.

Examples of the *Treponema pallidum* fused antigen of the present invention are a *Treponema pallidum* fused antigen in which at least two surface antigens of *Treponema pallidum* are fused, a *Treponema pallidum* fused antigen in which at least three surface antigens of *Treponema pallidum* are fused, and a *Treponema pallidum* fused antigen in which two to three surface antigens of *Treponema pallidum* are fused.

In the above-mentioned *Treponema pallidum* fused antigen of the present invention, at least two surface antigens, at least three surface antigens, or two to three surface antigens may have a molecular weight selected from 47 kDa, 17 kDa and 15 kDa.

Specific examples of the *Treponema pallidum* fused antigens of the present invention are *Treponema pallidum* fused antigens in which surface antigens thereof are fused in the order of the surface antigen with a molecular weight of 47 kDa, the surface antigen with a molecular weight of 17 kDa, and the surface antigen with a molecular weight of 15 kDa in view of the sequence from an N-terminus thereof to a C-terminus thereof, which may be referred to as 47-17-15 fused antigen; *Treponema pallidum* fused antigens in which surface antigens thereof are fused in the order of the surface antigen with a molecular weight of 47 kDa, the surface antigen with a molecular weight of 15 kDa, and the surface antigen with a molecular weight of 17 kDa in view of the sequence from an N-terminus thereof to a C-terminus thereof, which may be referred to as 47-15-17 fused antigen; *Treponema pallidum* fused antigens in which surface antigens thereof are fused in the order of the surface antigen with a molecular weight of 15 kDa, the surface antigen with a molecular weight of 17 kDa, and the surface antigen with a molecular weight of 47 kDa in view of the sequence from an N-terminus thereof to a C-terminus thereof, which may be referred to as 15-17-47 fused antigen; *Treponema pallidum* fused antigens in which surface antigens thereof are fused in the order of the surface antigen with a molecular weight of 15 kDa, the surface antigen with a molecular weight of 47 kDa, and the surface antigen with a molecular weight of 17 kDa in view of the sequence from an N-terminus thereof to a C-terminus thereof, which may be referred to as 15-47-17 fused antigen; *Treponema pallidum* fused antigens in which surface antigens thereof are fused in the order of the surface antigen with a molecular weight of 17 kDa, the surface antigen with a molecular weight of 15 kDa, and the surface antigen with a molecular weight of 47 kDa in view of the sequence from an N-terminus thereof to a C-terminus thereof, which may be referred to as 17-15-47 fused antigen; *Treponema pallidum* fused antigens in which surface antigens thereof are fused in the order of the surface antigen with a molecular weight of 17 kDa, the surface antigen with a molecular weight of 47 kDa, and the surface antigen with a molecular weight of 15 kDa in view of the sequence from an N-terminus thereof to a C-terminus thereof, which may be referred to as 17-47-15 fused antigen; *Treponema pallidum* fused antigens in which surface antigens thereof are fused in the order of the surface antigen with a molecular weight of 47 kDa, and the surface antigen with a molecular weight of 17 kDa in view of the sequence from an N-terminus thereof to a C-terminus thereof, which may be referred to as 47-17 fused antigen; *Treponema pallidum* fused antigens in which surface antigens thereof are fused in the order of the surface antigen with a molecular weight of 47 kDa, and the surface antigen with a molecular weight of 15 kDa in view of the sequence from an N-terminus thereof to a C-terminus thereof, which may be referred to as 47-15 fused antigen; *Treponema pallidum* fused antigens in which surface antigens thereof are fused in the order of the surface antigen with a molecular weight of 17 kDa, and the surface antigen with a molecular weight of 47 kDa in view of the sequence from an N-terminus thereof to a C-terminus thereof, which may be referred to as 17-47 fused antigen; *Treponema pallidum* fused antigens in which surface antigens thereof are fused in the order of the surface antigen with a molecular weight of 17 kDa, and the surface antigen with a molecular weight of 15 kDa in view of the sequence from an N-terminus thereof to a C-terminus thereof, which may be referred to as 17-15 fused antigen; *Treponema pallidum* fused antigens in which surface antigens thereof are fused in the order of the surface antigen with a molecular weight of 15 kDa, and the surface antigen with a molecular weight of 47 kDa in view of the sequence from an N-terminus thereof to a C-terminus thereof, which may be referred to as 15-47 fused antigen; *Treponema pallidum* fused antigens in which surface antigens thereof are fused in the order of the surface antigen with a molecular weight of 15 kDa, and the surface antigen with a molecular weight of 17 kDa in view of the sequence from an N-terminus thereof to a C-terminus thereof, which may be referred to as 15-17 fused antigen; *Treponema pallidum* fused antigens in which surface antigens thereof are fused in the order of the surface antigen with a molecular weight of 15 kDa, and the surface antigen with a molecular weight of 15 kDa in view of the sequence from an N-terminus thereof to a C-terminus thereof, which may be referred to as 15-15 fused antigen; *Treponema pallidum* fused antigens in which surface antigens thereof are fused in the order of the surface antigen with a molecular weight of 15 kDa, the surface antigen with a molecular weight of 15 kDa, and the surface antigen with a molecular weight of 15 kDa in view of the sequence from an N-terminus thereof to a C-terminus thereof, which may be referred to as 15-15-15 fused antigen; and *Treponema pallidum* fused antigens in which surface antigens thereof are fused in the order of the surface antigen with a molecular weight of 15 kDa, the surface antigen with a molecular weight of 15 kDa, the surface antigen with a molecular weight of 15 kDa, and the surface antigen with a molecular weight of 15 kDa in view of the sequence from an N-terminus thereof to a C-terminus thereof, which may be referred to as 15-15-15-15 fused antigen.

Generally, in an assay system of anti-Tp antibodies, a mixture of the main antigens of Tp such as 47K, 17K and 15K are used, so that the necessary antigens have to be separately purified.

In sharp contrast to this, when a fused antigen of the present invention is employed, the fused antigen contains a plurality of antigens, so that the fused antigen can be purified as a single antigen and is easily available.

Furthermore, 17K and 15K antigens are rarely expressed by using the respective genes which encode such antigens. Therefore, these antigens are expressed as fused proteins with a protein such as TRX or GST. However, a fused antigen expressed by a fused gene containing a heteroantigen other than Tp antigen may induce an unexpected non-specific reaction which is not derived from Tp antigen.

In sharp contrast to this, the antigen of the present invention is the fused antigen to which only Tp antigens are fused, and free of a heteroantigen other than Tp antigen, and therefore is an excellent antigen for specifically detecting the anti-Tp antibody.

It is known that in an antibody assay for the diagnosis of virus infection, that a fused antigen may be employed to which a plurality of kinds of antigens is fused (Hepatology, Vol. 14, p. 381–387, 1991).

In contrast to this, the fused antigen of the present invention exhibits a much higher reactivity with the anti-Tp antibody than the reactivity in the case where each surface antigen is individually allowed to react with the anti-Tp antibody, so that there can be provided an anti-Tp antibody assay method with unconventionally high assay sensitivity by use of said fused antigen in the assay system for the anti-Tp antibody.

Furthermore, in the present invention, the main surface antigens, i.e., the 17K and 15K surface antigens, can be expressed in a surprisingly increased quantity when they are converted into fused antigens in combination with the Tp antigens, even though 17K and 15K surface antigens are rarely expressed either by using the gene which encodes a 17K surface agent alone or by using a 15K surface antigen alone.

The fused antigens of the present invention can be used in an anti-Tp antibody assay. The anti-Tp antibody assay means an assay in which the above-mentioned fused antigen is used as the antigen for the assay of the anti-Tp antibody. As long as the assay is based on an immune reaction between the anti-Tp antibody in the specimen and the fused antigen, the reaction may be carried by any method.

Various immunoassays are known to those skilled in the art, which may be classified, based on the reaction mode, into an agglutination method, a nephelometry method, a sandwich method, and a competition method; and based on the kinds of labeled materials, into enzyme-labeled immunoassay, fluorescent labeled immunoassay, luminescent labeled immunoassay and radioimmunoassay.

Of these immunoassay methods, particularly preferable immunoassay methods are the agglutination method which does not require exclusive equipment, ELISA method based on the enzyme-labeled immunoassay, which is suitable for handling many specimens, and the luminescent labeled immunoassay which is developed so as to have high sensitivity and is highly automated.

When the fused antigen of the present invention is used for the assay of anti-Tp antibody, for example, in the case of the agglutination method, the fused antigen of the present invention is bound to carriers such as latex particles, gelatin particles or magnetic particles, and non-specific absorption sites thereof are blocked. The fused antigen-bound carriers are allowed to react with a specimen to be tested for a predetermined period of time, and the amount of the anti-Tp antibody in the specimen can be measured, using a detection index as the turbidity of the agglutination formed by the immune reaction or an agglutination image formed by the immune reaction.

In the ELISA method, the fused antigen of the present invention is bound to the wells of a micro titer plate, and the non-specific absorption sites thereof are blocked.

The specimen is then added to the wells of the fused antigen-bound micro titer plate and allowed to react with the fused antigen for a predetermined period of time. The wells are then washed, and an antihuman immuno-globulin labeled with an enzyme such as peroxidase is then allowed to react therewith. The wells are then washed, and an enzyme reaction is carried out with the addition of a substrate corresponding to the labeling enzyme, whereby the enzyme activity is measured. Thus, the amount of the anti-Tp antibody in the specimen can be measured.

The above-mentioned agglutination method and ELISA method are known in the field of this technology. However, the assay of the present invention is not necessarily limited to the above-mentioned methods.

Examples of the specimens for use in the assay of the present invention include humors and diluted humors, such as serum of human or animals, to be tested for the diagnosis of Tp.

Other features of this invention will become apparent in the course of the following description of reference examples, and exemplary embodiments which are given for illustration of the invention and are not intended to be limiting thereof.

REFERENCE EXAMPLE 1
[Preparation of Anti-47K Monoclonal Antibody, Anti-17K Monoclonal Antibody, and Anti-15K Monoclonal Antibody]

As a surface antigen of Tp, 47K was expressed in *Escherichia coli* and purified.

Spleen cells obtained from a mouse which was immunized with the above recombinant antigen, and mouse myeloma cells were subjected to cell fusion, whereby a hybridoma was prepared.

This hybridoma was cultured and allowed to react with the above-mentioned recombinant antigen by ELISA using the above recombinant antigen and by Western blotting using the above native antigen 47K, so that a hybridoma which is capable of reacting with both the recombinant antigen and the native antigen 47K was screened. The thus screened hybridoma was cloned and a cell line thereof was established.

The thus established clone was injected into the abdominal cavity of the mouse, and the ascites was obtained therefrom and purified, whereby an anti-47K monoclonal antibody (hereinafter referred to as 47KMab) was obtained.

GST17K in which GST was fused to the N-terminus of 17K was expressed in *Escherichia coli* and purified.

Spleen cells obtained from a mouse which was immunized with the above recombinant antigen, and mouse myeloma cells were subjected to cell fusion, whereby a hybridoma was prepared.

This hybridoma was cultured and allowed to react with the above-mentioned recombinant antigen by ELISA using the above recombinant antigen and by Western blotting using the above native antigen 17K, so that a hybridoma which is capable of reacting with both the recombinant antigen and the native antigen 17K was screened. The thus screened hybridoma was cloned and a cell line thereof was established.

The thus established clone was injected into the abdominal cavity of the mouse, and the ascites was obtained therefrom and purified, whereby an anti-17K monoclonal antibody (hereinafter referred to as 17KMab) was obtained.

GST15K in which GST was fused to the N-terminus of 15K was expressed in *Escherichia coli* and purified.

Spleen cells obtained from a mouse which was immunized with the above recombinant antigen, and mouse myeloma cells were subjected to cell fusion, whereby a hybridoma was prepared.

This hybridoma was cultured and allowed to react with the above-mentioned recombinant antigen by ELISA using the above recombinant antigen and by Western blotting using the above native antigen 15K, so that a hybridoma which is capable of reacting with both the recombinant antigen and the native antigen 15K was screened. The thus screened hybridoma was cloned and a cell line thereof was established.

The thus established clone was injected into the abdominal cavity of the mouse, and the ascites was obtained therefrom and purified, whereby an anti-15K monoclonal antibody (hereinafter referred to as 15KMab) was obtained.

REFERENCE EXAMPLE 2
[Preparation of Expression Vector pW6A]

The DNA sequence which encodes tac promoter and GST was removed from Vector pGEX2T made by Pharmacia Biotec Co., Ltd, and the DNA sequence from the T7 promotor to gene 10 to the multi-cloning site to the T7 transcriptional-terminator from pGEMEX-1 made by Promega Co., Ltd. was inserted into the above removed pGEX2T.

From the thus obtained vector, the DNA sequence of gene 10 was removed, and the lac operator synthesized on a DNA synthesiser (Trademark "Model 381A" made by Applied Biosystem Co., Ltd.) was inserted immediately after the T7 promotor, and the multi-cloning site was partly modified. The thus prepared expression vector was named "pW6A". FIG. 1 shows a detailed diagram of pW6A.

REFERENCE EXAMPLE 3
[Preparation of Primers for Preparation of Vectors for Expressing Varieties of Fused Antigens]

The following primers were synthesized on the DNA synthesiser (Trademark "Model 381A" made by Applied Biosystem Co., Ltd.) in order to prepare each expression vector for preparing each fused antigen in the following Examples 1 to 16 and Reference Example 4:

```
                              5'-------------------------------------------------3'
Primer 1 (Sense) (SEQ ID NO:1)
Nde I 47K-5' terminus 18 bases
TAGCC CATATG GGCTCGTCTCATCATGAG                                    (29 bases)
Primer 2 (Antisense)       (SEQ ID NO:2)
15K-5' terminus 17 bases 47K-3' terminus 20 bases
ATAGAACTAAATGAACA        AGACACACGGGATAGGACAC
                                                                   (37 bases)
Primer 3 (Sense) (SEQ ID NO:3)
15K-5' terminus 17 bases
TGTTCATTTAGTTCTATCCC                                               (20 bases)
Primer 4 (Antisense) (SEQ ID NO:4)
17K-5' terminus 15 bases           15K-3' terminus 20 bases
TGTGCACGAGACACA                 CCTGCTAATAATGGCTTCCT
                                                                   (35 bases)
Primer 5 (Sense) (SEQ ID NO:5)
17K-5' terminus 20 bases
TGTGTCTCGTGCACAACCGT                                               (20 bases)
Primer 6 (Antisense) (SEQ ID NO:6)
BamH I                                            17K-3' terminus 21 bases
GATCC GGATCC              CTA    TTTCTTTGTTTTTTTGAGCAC
                                 Termination Codon
                                                                   (35 bases)
Primer 7 (Sense) (SEQ ID NO:7)
Nde I 15K-5' terminus 18 bases
TAGCC CATATG TGTTCATTTAGTTCTATC                                    (29 bases)
Primer 8 (Sense) (SEQ ID NO:8)
Nde I 17K-5' terminus 18 bases
TAGCC CATATG TGTGTCTCGTGCACAACC                                    (29 bases)
Primer 9 (Antisense) (SEQ ID NO:9)
BamH I 15K-3'                                          terminus 17 bases
GATCC GGATCC              CTA                     CCTGCTAATAATGGCTT
                           Termination Codon
                                                                   (31 bases)
Primer 10 (Antisense) (SEQ ID NO:10)
BamH I 47K-3'                                          terminus 17 bases
GATCC GGATCC              CTA                     AGACACACGGGATAGGA
                           Termination Codon
                                                                   (31 bases)
Primer 11 (Sense) (SEQ ID NO:11)
Sal I 15K-5' terminus 18 bases
CGAGGC GTCGAC TGTTCATTTAGTTCTATC                                   (30 bases)
Primer 12 (Sense) (SEQ ID NO:12)
Sal I 47K-5' terminus 18 bases
GAAC GTCGAC TGTGGCTCGTCTCATCAT                                     (28 bases)
Primer 13 (Antisense) (SEQ ID NO:13)
Xho I 47K-3' terminus 18 bases
CTTG CTCGAG AGACACACGGGATAGGAC                                     (28 bases)
Primer 14 (Sense) (SEQ ID NO:14)
Sal I 17K-5' terminus 18 bases
AGTA GTCGAC TGTGTCTCGTGCACAACC                                     (28 bases)
Primer 15 (Antisense) (SEQ ID NO:15)
Xho I 17K-3' terminus 21 bases
CAGA CTCGAG TTTCTTTGTTTTTTTGAGCAC                                  (31 bases)
Primer 16 (Antisense) (SEQ ID NO:16)
Sal I 17K-3' terminus 21 bases
CAGA GTCGAC TTTCTTTGTTTTTTTGAGCAC                                  (31 bases)
Primer 17 (Antisense) (SEQ ID NO:17)
Sal I 15K-3' terminus 18 bases
GCTA GTCGAC CCTGCTAATAATGGCTTC                                     (28 bases)
Primer 18 (Antisense) (SEQ ID NO:18)
Sac I 47K-3' terminus 20 bases
CGTA GAGCTC AGACACACGGGATAGGACAC                                   (30 bases)
Primer 19 (Sense) (SEQ ID NO:19)
Sac I 17K-5' terminus 20 bases
TAGC GAGCTC TGTGTCTCGTGCACAACCGT                                   (30 bases)
Primer 20 (Antisense) (SEQ ID NO:20)
BamH I                    Base for encoding 9 amino acids
GATCC GGATCC              CTA  AGACACACGGGATAGGACACCCCTCTT
                               termination Codon
                                    47K-3' terminus 18 bases
                                    CTGGGCCACTACCTTCGC
                                                                   (59 bases)
Primer 21 (Antisense) (SEQ ID NO:21)
Sal I 47K-3' terminus 18 bases
CTCTT GTCGAC AGACACACGGGATAGGAC                                    (29 bases)
Primer 22 (Antisense) (SEQ ID NO:22)
BamH I 15K-3' terminus 18 bases
CCGG GGATCC CCTGCTAATAATGGCTTC                                     (28 bases)
```

-continued

```
Primer 23 (Sense) (SEQ ID NO:23)
BamH I 15K-5' terminus 18 bases
CCGG GGATCC TGTTCATTTAGTTCTATC                              (28 bases)
Primer 24 (Antisense) (SEQ ID NO:24)
Kpn I                              15K-3' terminus 18 bases
CCGG GGTACC             CTA   CCTGCTAATAATGGCTTC
                        Termination Codon
                                                            (31 bases)
Primer 25 (Antisense) (SEQ ID NO:25)
Kpn I 15K-3' terminus 18 bases
CCGG GGTACC CCTGCTAATAATGGCTTC                              (28 bases)
Primer 26 (Sense) (SEQ ID NO:26)
Kpn I 15K-5' terminus 18 bases
CCGG GGTACC TGTTCATTTAGTTCTATC                              (28 bases)
Primer 27 (Antisense) (SEQ ID NO:27)
Hind III                                       15K-3' terminus 15 bases
CCGG AAGCTT             CTA   CCTGCTAATAATGGC
                        Termination Codon
                                                            (28 bases)
Primer 28 (Antisense) (SEQ ID NO:28)
EcoR I 17K-3' terminus 21 bases
GACT GAATTC TTTCTTTGTTTTTTTGAGCAC                           (31 bases)
Primer 29 (Sense) (SEQ ID NO:29)
EcoR                                        15K-5' terminus 21 bases
GGTG GAATTC TGTTCATTTAGTTCTATCCCG
                                                            (31 bases)
```

REFERENCE EXAMPLE 4
[Preparation of Tp47K, 17K and 15K Genes]

*Treponema pallium* (Nicols strain), which was subcultured in the testes of rabbit, was purified by Percoll density-gradient centrifugation (Sex. Transm. Dis., Vol. 11, p. 275–286, 1984), and a genomic DNA was extracted by SDS-proteinase K/phenol.chloroform method.

By the polymerase chain reaction (PCR) method, the DNA fragment which encodes 15K was amplified, using Primer 7 prepared in Reference Example 3 as a sense primer, Primer 9 prepared in Reference Example 3 as an antisense primer, and the above extracted genomic DNA as a template (Molecular Microbiology, Vol. 4, p. 1371–1379, 1990).

A DNA fragment which encodes 17K was amplified, using Primer 8 prepared in Reference Example 3 as a sense primer, and Primer 6 prepared in Reference Example 3 as an antisense primer (Infection and Immunity, Vol. 61, p. 1202–1210, 1993).

Furthermore, a DNA fragment which encodes 47K was amplified, using Primer 1 prepared in Reference Example 3 as a sense primer, and Primer 20 prepared in Reference Example 3 as an antisense primer (Infection and Immunity, Vol. 60, p. 1568–1576, 1992).

Figure 2:
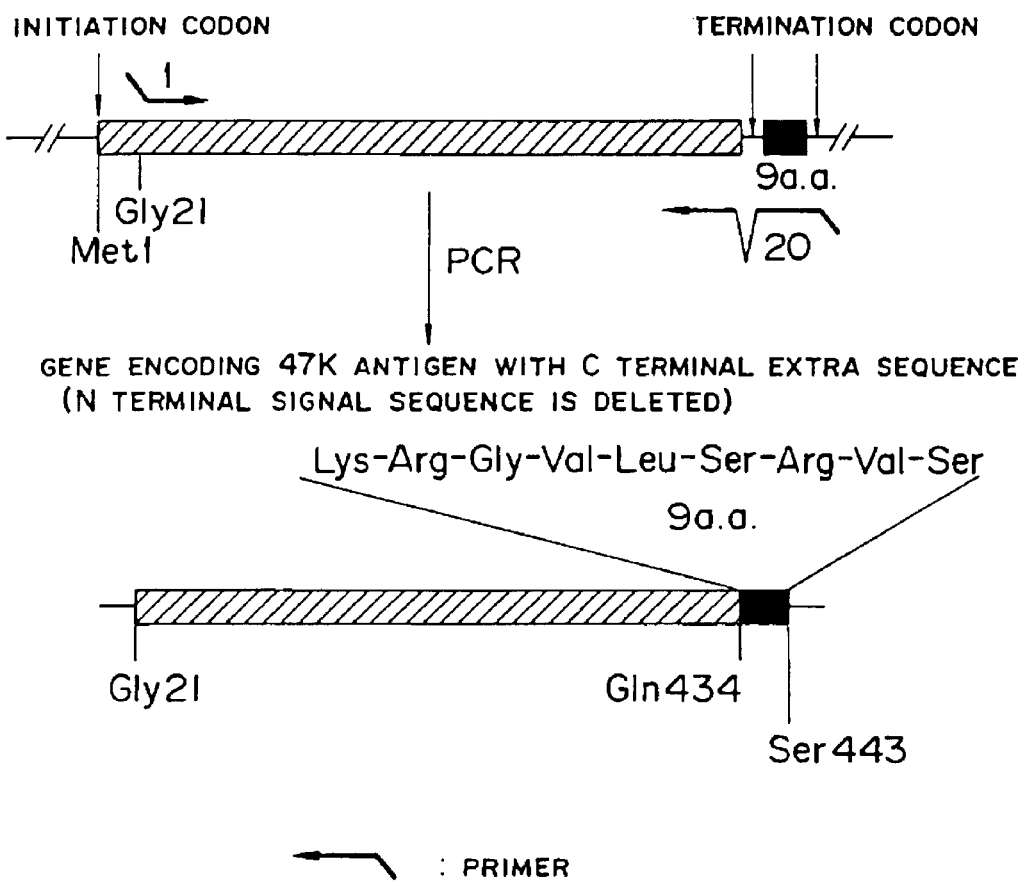
FIG. 2 is a diagram showing the procedure for preparing a gene which encodes a 47K antigen.

In Infection and Immunity, Vol. 60, p. 1568–1576, 1992, it is reported that it is possible that 9 amino acids are further bonded to the C-terminus of 434 amino acids in 47K. Therefore, as shown in FIG. 2, at the amplification of the DNA fragment of 47K, a DNA fragment which encodes 47K was prepared by adding a DNA sequence corresponding to the 9 amino acids to the antisense primer to be used (SEQ ID NO: 30).

Figure 3:
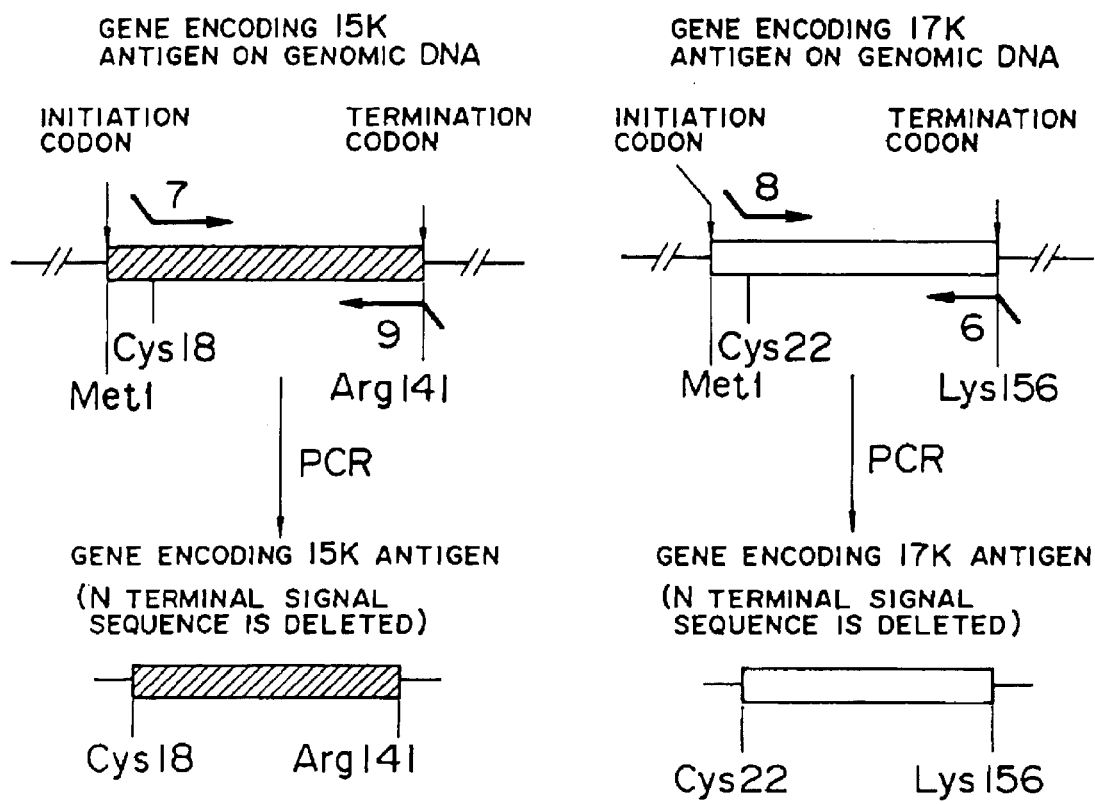
FIG. 3 is a diagram showing the procedure for preparing a gene which encodes a 15K antigen and a 17K antigen.

FIG. 3 shows a DNA fragment for encoding 15K and a DNA fragment for encoding 17K.

EXAMPLE 1
[Preparation of Expression Vector for 15-17 Fused Antigen]

(a) As a sense primer, Primer 7 prepared in Reference Example 3 was selected, and as an antisense primer, Primer 4 prepared in Example 3 was selected.

A mixture of each of the above-mentioned Primers 7 and 4 at a final concentration of 1 μM, 0.1 ng of the 15K gene prepared in Reference Example 4, and 2.5 units of Taq polymerase (made by TaKaRa Co., Ltd.) was subjected to the PCR under a heat application cycle of 94° C. for 1 minute, 55° C. for 2 minutes and 72° C. for 3 minutes, with this heat application cycle being repeated 30 times, whereby a DNA fragment 1 was prepared.

(b) As a sense primer, Primer 5 prepared in Reference Example 3 was selected, and as an antisense primer, Primer 6 prepared in Example 3 was selected.

A mixture of each of the above-mentioned Primers 5 and 6 at a final concentration of 1 μM, 0.1 ng of the 17K gene prepared in Reference Example 4, and 2.5 units of Taq polymerase (made by TaKaRa Co., Ltd.) was subjected to PCR under the same heat application cycle as in the step (a) in Example 1, with this heat application cycle being repeated 30 times, whereby a DNA fragment 2 was prepared.

(c) A mixture of 1 ng of the DNA fragment 1 prepared in the step (a) in Example 1, 1 ng of the DNA fragement 2, each of Primers 7 and 6 prepared in Reference Example 3 at a final concentration of 1 μM, and 2.5 units of the above-mentioned Taq polymerase (made by TaKaRa Co., Ltd.) was subjected to the PCR under a heat application cycle of 94° C. for 1 minute, 55° C. for 2 minutes and 72° C. for 3 minutes, with this heat application cycle being repeated 40 times, whereby a DNA fragment for encoding a 15-17 fused antigen was prepared.

(d) The pW6A prepared in Reference Example 3 was subjected to digestion at 37° C. for 1 hour with 5 units of Nde I (made by New England Biolab Co., Ltd.) and 5 units of BamH I (made by New England Biolab Co., Ltd.).

The 15-17 fused antigen gene prepared in the step (c) in Example 1 was also subjected to digestion at 37° C. for 1 hour with 5 units of Nde I (made by New England Biolab Co., Ltd.) and 5 units of BamH I (made by New England Biolab Co., Ltd.).

(e) The pW6A and 15-17 fused antigen gene, which were subjected to digestion in the step (d) in Example 1, were ligated at 16° C. for 2 hours by use of Ligation Kit ver. 1 (made by TaKaRa Co., Ltd.). After the completion of this reaction, *Escherichia coli* DH5α, which is a competent cell prepared by Hanahan method, was transformed by use of the above reaction mixture. The thus transformed *Escherichia coli* cells were then plated on an LB agar plate containing 50

μg/ml ampicillin and incubated at 37° C. overnight. From the colonies of the ampicillin-resistant *Escherichia coli* cells thus produced, the transformant was selected carrying an expression vector for a 15-17 fused antigen with which a 15-17 fused antigen gene was integrated. The thus selected transformant was then cultured in an ampicillin-containing LB liquid culture medium, with shaking at 37° C. overnight. The desired transformant clone was harvested, from which a desired vector was purified by an alkali SDS method.

Figure 4:
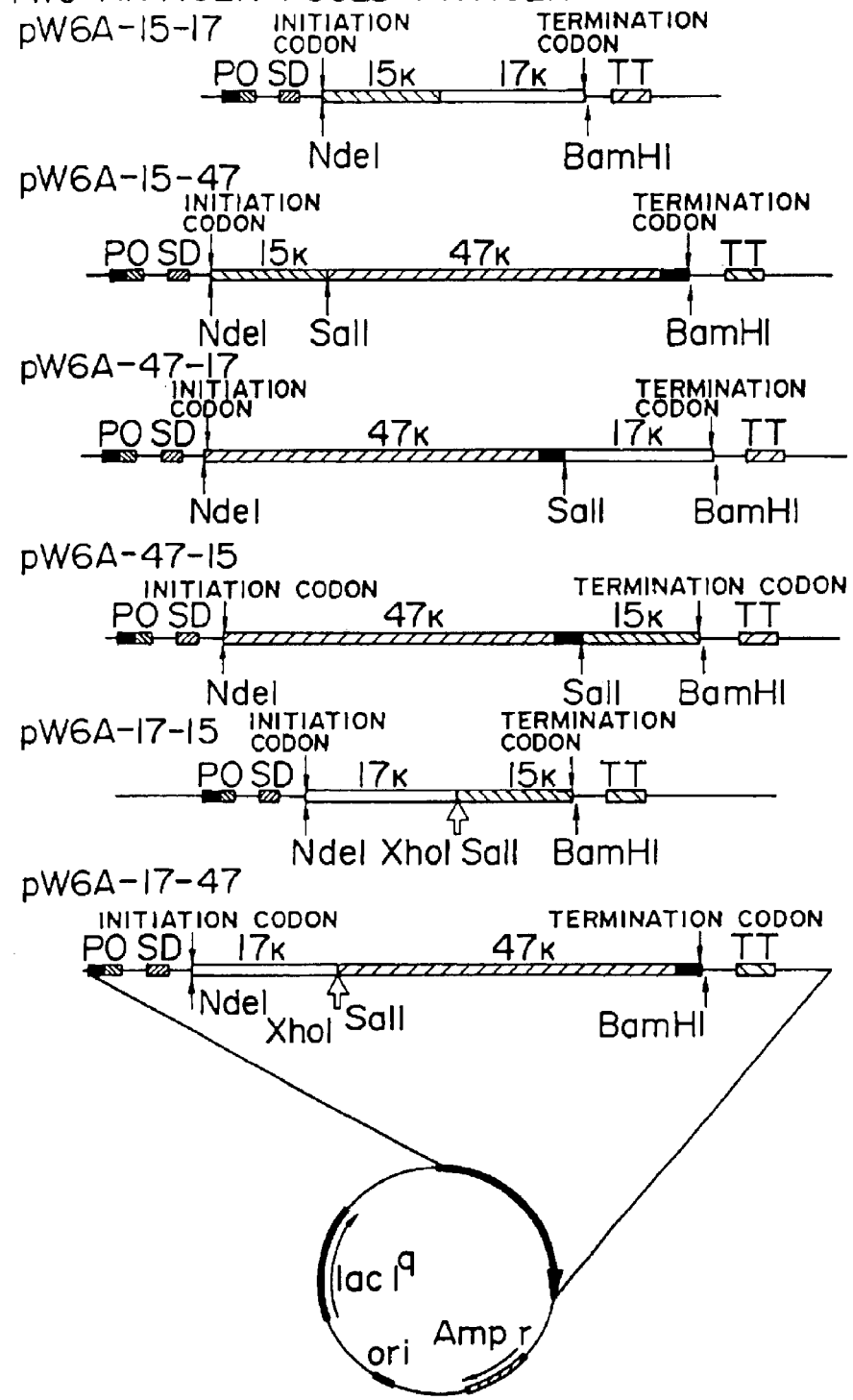
FIG. 4 is a detailed diagram of an expression vector for a two-antigen fused antigen.

The results are shown in FIG. 4.

EXAMPLE 2

[Preparation of Expression Vector for 15-47 Fused Antigen]

(a) As a sense primer, Primer 7 prepared in Reference Example 3 was selected, and as an antisense primer, Primer 17 prepared in Example 3 was selected.

A mixture of each of the above-mentioned Primers 7 and 17 at a final concentration of 1 μM, 0.1 ng of the 15K gene prepared in Reference Example 4, and 2.5 units of Taq polymerase (made by TaKaRa Co., Ltd.) was subjected to PCR under a heat application cycle of 94° C. for 1 minute, 55° C. for 2 minutes and 72° C. for 3 minutes, with this heat application cycle being repeated 30 times, whereby a DNA fragment 3 was prepared.

(b) The DNA fragment 3 prepared in the step (a) of Example 2 was subjected to digestion at 37° C. for 1 hour with 5 units of Nde I (made by New England Biolab Co., Ltd.) and 5 units of Sal I (made by Toyobo Co., Ltd.).

The pW6A prepared in Reference Example 2 was also subjected to digestion at 37° C. for 1 hour with 5 units of Nde I (made by New England Biolab Co., Ltd.) and 5 units of Sal I (made by Toyobo Co., Ltd.).

After these reactions, the DNA fragment 3 was inserted into the pW6A prepared in Reference Example 2 under the same conditions as in the step (e) in Example 1.

(c) As a sense primer, Primer 12 prepared in Reference Example 3 was selected, and as an antisense primer, Primer 10 prepared in Example 3 was selected.

A mxture of each of the above-mentioned Primers 12 and 10 at a final concentration of 1 μM, 0.1 ng of the 47K gene prepared in Reference Example 4, and 2.5 units of the above-mentioned Taq polymerase (made by TaKaRa Co., Ltd.) was subjected to the PCR under a heat application cycle of 94° C. for 1 minute, 55° C. for 2 minutes and 72° C. for 3 minutes, with this heat application cycle being repeated 30 times, whereby a DNA fragment 4 was prepared.

(d) The DNA fragment 3 inserted in pW6A prepared in the step (b) of Example 2 was subjected to digestion at 37° C. for 1 hour with 5 units of the above-mentioned Sal I and 5 units of the above-mentioned BamH I.

The DNA fragment 4 prepared in the step (c) of Example 2 was also subjected to digestion at 37° C. for 1 hour with 5 units of the above-mentioned Sal I and 5 units of the above-mentioned BamH I.

After these reactions, the DNA fragment 4 was inserted into the DNA fragment 3 inserted pW6A under the same conditions as in the step (e) in Example 1, whereby an expression vector for the 15-47 fused antigen was obtained.

The results are shown in FIG. 4.

EXAMPLE 3

[Preparation of Expression Vector for 17-47 Fused Antigen]

(a) As a sense primer, Primer 8 prepared in Reference Example 3 was selected, and as an antisense primer, Primer 15 prepared in Example 3 was selected.

A mixture of each of the above-mentioned Primers 8 and 15 at a final concentration of 1 μM, 0.1 ng of the 17K gene prepared in Reference Example 4, and 2.5 units of the above-mentioned Taq polymerase was subjected to PCR under a heat application cycle of 94° C. for 1 minute, 55° C. for 2 minutes and 72° C. for 3 minutes, with this heat application cycle being repeated 30 times, whereby a DNA fragment 5 was prepared.

(b) The DNA fragment 5 prepared in the step (a) of Example 3 was subjected to digestion at 37° C. for 1 hour with 5 units of the above-mentioned Nde I and 5 units of Xho I (made by Toyobo Co., Ltd.).

The pW6A prepared in Reference Example 2 was also subjected to digestion at 37° C. for 1 hour with 5 units of the above-mentioned Nde I and 5 units of the above-mentioned Xho I.

After these reactions, the DNA fragment 5 was inserted into the pW6A under the same conditions as in the step (e) in Example 1.

(c) The DNA fragment 4 obtained in the step (c) of Example 2 was subjected to digestion at 37° C. for 1 hour with 5 units of the above-mentioned Sal I and 5 units of the above-mentioned BamH I.

The DNA fragment 5 inserted in pW6A obtained in the step (b) of Example 3 was subjected to digestion at 37° C. for 1 hour with 5 units of the above-mentioned Xho I and 5 units of the above-mentioned BamH I.

After these reactions, the DNA fragment 4 was inserted into the DNA fragment 5 inserted pW6A under the same conditions as in the step (e) in Example 1, whereby an expression vector for the 17-47 fused antigen was prepared.

The results are shown in FIG. 4.

EXAMPLE 4

[Preparation of Expression Vector for 17-15 Fused Antigen]

(a) As a sense primer, Primer 11 prepared in Reference Example 3 was selected, and as an antisense primer, Primer 9 prepared in Example 3 was selected.

A mixture of each of the above-mentioned Primers 11 and 9 at a final concentration of 1 μM, 0.1 ng of the 15K gene prepared in Reference Example 4, and 2.5 units of the above-mentioned Taq polymerase was subjected to the PCR under a heat application cycle of 94° C. for 1 minute, 55° C. for 2 minutes and 72° C. for 3 minutes, with this heat application cycle being repeated 30 times, whereby a DNA fragment 6 was prepared.

(b) The DNA fragment 6 prepared in the step (a) of Example 4 was subjected to digestion at 37° C. for 1 hour with 5 units of the above-mentioned Sal I and 5 units of the above-mentioned BamH I.

The DNA fragment 5 inserted in pW6A prepared in the step (b) of Example 3 was subjected to digestion at 37° C. for 1 hour with 5 units of the above-mentioned Xho I and 5 units of the above-mentioned BamH I.

After these reactions, the DNA fragment 6 was inserted into the DNA fragment 5 inserted pW6A under the same conditions as in the step (e) in Example 1, whereby an expression vector for the 17-15 fused antigen was prepared.

The results are shown in FIG. 4.

EXAMPLE 5

[Preparation of Expression Vector for 47-15 Fused Antigen]

(a) As a sense primer, Primer 1 prepared in Reference Example 3 was selected, and as an antisense primer, Primer 21 prepared in Example 3 was selected.

A mixture of each of the above-mentioned Primers 1 and 21 at a final concentration of 1 μM, 0.1 ng of the 47K gene prepared in Reference Example 4, and 2.5 units of the above-mentioned Taq polymerase was was subjected to the PCR under a heat application cycle of 94° C. for 1 minute, 55° C. for 2 minutes and 72° C. for 3 minutes, with this heat application cycle being repeated 30 times, whereby a DNA fragment 7 was prepared.

(b) The DNA fragment 7 prepared in the step (a) of Example 5 was subjected to digestion at 37° C. for 1 hour with 5 units of the above-mentioned Nde I and 5 units of the above-mentioned Sal I.

The pW6A prepared in Reference Example 2 was also subjected to digestion at 37° C. for 1 hour with 5 units of the above-mentioned Nde I and 5 units of the above-mentioned Sal I.

After these reactions, the DNA fragment 7 was inserted into the pW6A under the same conditions as in the step (e) in Example 1.

(c) The DNA fragment 6 prepared in the step (a) of Example 4 was subjected to digestion at 37° C. for 1 hour with 5 units of the above-mentioned Sal I and 5 units of the above-mentioned BamH I.

The DNA fragment 7 inserted in pW6A prepared in the step (b) of Example 5 was also subjected to digestion at 37° C. for 1 hour with 5 units of the above-mentioned Sal I and 5 units of the above-mentioned BamH I.

After these reactions, the DNA fragment 6 was inserted into the DNA fragment 7 inserted in pW6A under the same conditions as in the step (e) in Example 1, whereby an expression vector for the 47-15 fused antigen was prepared.

The results are shown in FIG. 4.

EXAMPLE 6

[Preparation of Expression Vector for 47-17 Fused Antigen]

(a) As a sense primer, Primer 14 prepared in Reference Example 3 was selected, and as an antisense primer, Primer 6 prepared in Example 3 was selected.

A mixture of each of the above-mentioned Primers 14 and 6 at a final concentration of 1 $\mu$M, 0.1 ng of the 17K gene prepared in Reference Example 4, and 2.5 units of the above-mentioned Taq polymerase was subjected to the PCR under a heat application cycle of 94° C. for 1 minute, 55° C. for 2 minutes and 72° C. for 3 minutes, with this heat application cycle being repeated 30 times, whereby a DNA fragment 8 was prepared.

(b) The DNA fragment 8 prepared in the step (a) of Example 6 was subjected to digestion at 37° C. for 1 hour with 5 units of the above-mentioned Sal I and 5 units of the above-mentioned BamH I.

The DNA fragment 7 inserted pW6A prepared in the step (b) of Example 5 was subjected to digestion at 37° C. for 1 hour with 5 units of the above-mentioned Sal I and 5 units of the above-mentioned BamH I.

After these reactions, the DNA fragment 8 was inserted into the DNA fragment 7 inserted pW6A under the same conditions as in the step (e) in Example 1, whereby an expression vector for the 47-17 fused antigen was prepared.

The results are shown in FIG. 4.

EXAMPLE 7

[Preparation of Expression Vector for 47-15-17 Fused Antigen]

(a) As a sense primer, Primer 11 prepared in Reference Example 3 was selected, and as an antisense primer, Primer 6 prepared in Example 3 was selected.

A mixture of each of the above-mentioned Primers 11 and 6 at a final concentration of 1 $\mu$M, 0.1 ng of the expression vector for the 15-17 fused antigen prepared in Example 1, and 2.5 units of the above-mentioned Taq polymerase was subjected to PCR under a heat application cycle of 94° C. for 1 minute, 55° C. for 2 minutes and 72° C. for 3 minutes, with this heat application cycle being repeated 30 times, whereby a DNA fragment 9 was prepared.

(b) The DNA fragment 8 prepared in the step (a) of Example 7 was subjected to digestion at 37° C. for 1 hour with 5 units of the above-mentioned Sal I and 5 units of the above-mentioned BamH I.

The DNA fragment 7 inserted in pW6A prepared in the step (b) of Example 5 was also subjected to digestion at 37° C. for 1 hour with 5 units of the above-mentioned Sal I and 5 units of the above-mentioned BamH I.

After these reactions, the DNA fragment 9 was inserted into the DNA fragment 7 inserted pW6A under the same conditions as in the step (e) in Example 1, whereby an expression vector for 47-15-17 fused antigen was prepared.

The results are shown in FIG. 5.

EXAMPLE 8

[Preparation of Expression Vector for 17-47-15 Fused Antigen]

(a) As a sense primer, Primer 12 prepared in Reference Example 3 was selected, and as an antisense primer, Primer 2 prepared in Example 3 was selected.

A mixture of each of the above-mentioned Primers 7 and 17 at a final concentration of 1 $\mu$M, 0.1 ng of the 47K gene prepared in Reference Example 4, and 2.5 units of the above-mentioned Taq polymerase was subjected to PCR under a heat application cycle of 94° C. for 1 minute, 55° C. for 2 minutes and 72° C. for 3 minutes, with this heat application cycle being repeated 30 times, whereby a DNA fragment 10 was prepared.

(b) As a sense primer, Primer 3 prepared in Reference Example 3 was selected, and as an antisense primer, Primer 9 prepared in Example 3 was selected.

A mixture of each of the above-mentioned Primers 3 and 9 at a final concentration of 1 $\mu$M, 0.1 ng of the 15K gene prepared in Reference Example 4, and 2.5 units of the above-mentioned Taq polymerase was subjected to the PCR under a heat application cycle of 94° C. for 1 minute, 55° C. for 2 minutes and 72° C. for 3 minutes, with this heat application cycle being repeated 30 times, whereby a DNA fragment 11 was prepared.

(c) A mixture of 1 ng of the DNA fragment 10 prepared in the step (a) of Example 8, 1 ng of the DNA fragment 11 prepared in the step (b) of Example 8, each of the Primers 12 and 9 at a final concentration of 1 $\mu$M, and 2.5 units of the above-mentioned Taq polymerase was subjected to PCR under a heat application cycle of 94° C. for 1 minute, 55° C. for 2 minutes and 72° C. for 3 minutes, with this heat application cycle being repeated 30 times, whereby a gene for encoding the 47-15 fused gene was prepared.

(d) The gene encoding the 47-15 fused gene prepared in the step (c) of Example 8 was subjected to digestion at 37° C. for 1 hour with 5 units of the above-mentioned Sal I and 5 units of the above-mentioned BamH.

The DNA fragment 5 inserted pW6A prepared in the step (b) of Example 3 was also subjected to digestion at 37° C. for 1 hour with 5 units of the above-mentioned Xho I and 5 units of the above-mentioned BamH I.

After these reactions, a gene for encoding the 47-15 fused antigen was inserted into the DNA fragment 5 inserted pW6A under the same conditions as in the step (e) in Example 1, whereby an expression vector for the 17-47-15 fused antigen was obtained.

The results are shown in FIG. 5.

EXAMPLE 9

[Preparation of Expression Vector for 17-15-47 Fused Antigen]

(a) As a sense primer, Primer 8 prepared in Reference Example 3 was selected, and as an antisense primer, Primer 17 prepared in Example 3 was selected.

A mixture of each of the above-mentioned Primers 8 and 17 at a final concentration of 1 μM, 0.1 ng of the expression vector for the 17-15 fused antigen prepared in Example 4, and 2.5 units of the above-mentioned Taq polymerase was subjected to PCR under a heat application cycle of 94° C. for 1 minute, 55° C. for 2 minutes and 72° C. for 3 minutes, with this heat application cycle being repeated 30 times, whereby a DNA fragment 12 was prepared.

(b) The DNA fragment 12 prepared in the step (a) of Example 9 was subjected to digestion at 37° C. for 1 hour with 5 units of the above-mentioned Nde I and 5 units of the above-mentioned Sal I.

The pW6A prepared in Reference Example 2 was also subjected to digestion at 37° C. for 1 hour with 5 units of the above-mentioned Nde I and 5 units of the above-mentioned Sal I.

After these reactions, the DNA fragment 12 was inserted into pW6A under the same conditions as in the step (e) in Example 1.

(c) The DNA fragment 4 prepared in the step (c) of Example 2 was subjected to digestion at 37° C. for 1 hour with 5 units of the above-mentioned Sal I and 5 units of the above-mentioned BamH I.

The DNA fragment 12 inserted in pW6A prepared in the step (b) of Example 9 was also subjected to digestion at 37° C. for 1 hour with 5 units of the above-mentioned Sal I and 5 units of the above-mentioned BamH I.

After these reactions, the DNA fragment 4 was inserted into the DNA fragment 12 inserted pW6A under the same conditions as in the step (e) in Example 1, whereby an expression vector for a 17-15-47 fused antigen was prepared.

The results are shown in FIG. 5.

EXAMPLE 10
[Preparation of Expression Vector for 15-47-17 Fused Antigen]

(a) As a sense primer, Primer 12 prepared in Reference Example 3 was selected, and as an antisense primer, Primer 13 prepared in Example 3 was selected.

A mixture of each of the above-mentioned Primers 12 and 13 at a final concentration of 1 μM, 0.1 ng of the 47K gene prepared in Reference Example 4, and 2.5 units of the above-mentioned Taq polymerase was subjected to PCR under a heat application cycle of 94° C. for 1 minute, 55° C. for 2 minutes and 72° C. for 3 minutes, with this heat application cycle being repeated 30 times, whereby a DNA fragment 13 was prepared.

(b) The DNA fragment 13 prepared in the step (a) of Example 10 was subjected to digestion at 37° C. for 1 hour with 5 units of the above-mentioned Sal I and 5 units of the above-mentioned Xho I.

The pW6A prepared in Reference Example 2 was also subjected to digestion at 37° C. for 1 hour with 5 units of the above-mentioned Sal I and 5 units of the above-mentioned Xho I.

After these reactions, the DNA fragment 13 was inserted into the pW6A under the same conditions as in the step (e) in Example 1.

(c) The DNA fragment 8 prepared in Example 6 was subjected to digestion at 37° C. for 1 hour with 5 units of the above-mentioned Sal I and 5 units of the above-mentioned BamH.

The DNA fragment 13 inserted pW6A prepared in the step (b) of Example 10 was also subjected to digestion at 37° C. for 1 hour with 5 units of the above-mentioned Xho I and 5 units of the above-mentioned BamH I.

After these reactions, the DNA fraction 8 was inserted into the DNA fragment 13 inserted pW6A under the same conditions as in the step (e) in Example 1, whereby a DNA fragment 13-8 inserted pW6A was prepared.

(d) The DNA fragment 3 prepared in the step (a) of Example 2 was subjected to digestion at 37° C. for 1 hour with 5 units of the above-mentioned Nde I and 5 units of the above-mentioned Sal I.

The DNA fragment 13-8 inserted pW6A prepared in the step (c) of Example 10 was also subjected to digestion at 37° C. for 1 hour with 5 units of the above-mentioned Nde I and 5 units of the above-mentioned Sal I.

After these reactions, the DNA fragment 3 was inserted into the DNA fragment 13-8 inserted pW6A under the same conditions as in the step (e) in Example 1, whereby an expression vector for a 15-47-17 fused antigen was prepared.

EXAMPLE 11
[Preparation of Expression Vector for 15-17-47 Fused Antigen]

(a) As a sense primer, Primer 7 prepared in Reference Example 3 was selected, and as an antisense primer, Primer 16 prepared in Example 3 was selected.

A mixture of each of the above-mentioned Primers 7 and 16 at a final concentration of 1 μM, 0.1 ng of the expression vector for the 15-17 fused antigen prepared in Example 1, and 2.5 units of the above-mentioned Taq polymerase was subjected to PCR under a heat application cycle of 94° C. for 1 minute, 55° C. for 2 minutes and 72° C. for 3 minutes, with this heat application cycle being repeated 30 times, whereby a DNA fragment 14 was prepared.

(b) The DNA fragment 14 prepared in the step (a) of Example 11 was subjected to digestion at 37° C. for 1 hour with 5 units of the above-mentioned Nde I and 5 units of the above-mentioned Sal I.

The pW6A prepared in Reference Example 2 was also subjected to digestion at 37° C. for 1 hour with 5 units of the above-mentioned Nde I and 5 units of the above-mentioned Sal I.

After these reactions, the DNA fragment 14 was inserted into the pW6A under the same conditions as in the step (e) in Example 1.

(c) The DNA fragment 4 prepared in the step (c) of Example 2 was subjected to digestion at 37° C. for 1 hour with 5 units of the above-mentioned Sal I and 5 units of the above-mentioned BamH.

The DNA fragment 14 inserted pW6A prepared in the step (b) of Example 11 was also subjected to digestion at 37° C. for 1 hour with 5 units of the above-mentioned Sal I and 5 units of the above-mentioned BamH I.

After these reactions, the DNA fraction 4 was inserted into the DNA fragment 14 inserted pW6A under the same conditions as in the step (e) in Example 1, whereby an expression vector for a 15-17-47 fused antigen was prepared.

The results are shown in FIG. 5.

EXAMPLE 12
[Preparation of Expression Vector for 47-17-15 Fused Antigen]

(a) As a sense primer, Primer 1 prepared in Reference Example 3 was selected, and as an antisense primer, Primer 18 prepared in Example 3 was selected.

A mixture of each of the above-mentioned Primers 1 and 18 at a final concentration of 1 μM, 0.1 ng of the 47K gene prepared in Reference Example 4, and 2.5 units of the above-mentioned Taq polymerase was subjected to the PCR under a heat application cycle of 94° C. for 1 minute, 55° C. for 2 minutes and 72° C. for 3 minutes, with this heat application cycle being repeated 30 times, whereby a DNA fragment 15 was prepared.

(b) The DNA fragment 15 prepared in the step (a) of Example 12 was subjected to digestion at 37° C. for 1 hour with 5 units of the above-mentioned Sac I (made by Toyobo Co., Ltd.) and then subjected to digestion at 37° C. for 1 hour with 5 units of the above-mentioned Nde I.

The pW6A prepared in Reference Example 2 was also subjected to digestion at 37° C. for 1 hour with 5 units of the above-mentioned Sac I and then subjected to digestion at 37° C. for 1 hour with 5 units of the above-mentioned Nde I.

After these reactions, the DNA fragment 15 was inserted into the pW6A under the same conditions as in the step (e) in Example 1.

(c) As a sense primer, Primer 19 prepared in Reference Example 3 was selected, and as an antisense primer, Primer 28 prepared in Example 3 was selected.

A mixture of each of the above-mentioned Primers 19 and 28 at a final concentration of 1 µM, 0.1 ng of the 17K gene prepared in Reference Example 4, and 2.5 units of the above-mentioned Taq polymerase was subjected to PCR under a heat application cycle of 94° C. for 1 minute, 55° C. for 2 minutes and 72° C. for 3 minutes, with this heat application cycle being repeated 30 times, whereby a DNA fragment 16 was prepared.

(d) As a sense primer, Primer 29 prepared in Reference Example 3 was selected, and as an antisense primer, Primer 9 prepared in Example 3 was selected.

A mixture of each of the above-mentioned Primers 29 and 9 at a final concentration of 1 µM, 0.1 ng of the 15K gene prepared in Reference Example 4, and 2.5 units of the above-mentioned Taq polymerase was subjected to PCR under a heat application cycle of 94° C. for 1 minute, 55° C. for 2 minutes and 72° C. for 3 minutes, with this heat application cycle being repeated 30 times, whereby a DNA fragment 17 was prepared.

(e) The DNA fragment 16 prepared in the step (c) of Example 12 was subjected to digestion at 37° C. for 1 hour with 5 units of the above-mentioned Sac I and then subjected to digestion at 37° C. for 1 hour with 5 units of EcoR I (made by Toyobo Co., Ltd.).

The DNA fragment 17 prepared in the step (d) of Example 12 was subjected to digestion at 37° C. for 1 hour with 5 units of the above-mentioned EcoR I and 5 units of the above-mentioned BamH I.

The DNA fragment 15 inserted pW6A prepared in the step (b) of Example 12 was subjected to digestion at 37° C. for 1 hour with 5 units of the above-mentioned Sac I and then subjected to digestion at 37° C. for 1 hour with 5 units of the above-mentioned BamH I.

After these reactions, the DNA fragment 16 and the DNA fragment 17 were simultaneously inserted into the DNA fragment 15 inserted pW6A under the same conditions as in the step (e) in Example 1, whereby an expression vector for a 47-17-15 fused antigen was obtained. The results are shown in FIG. 5.

EXAMPLE 13
[Preparation of Expression Vector for 15 Fused Antigen]

(a) As a sense primer, Primer 7 prepared in Reference Example 3 was selected, and as an antisense primer, Primer 9 prepared in Example 3 was selected.

A mixture of each of the above-mentioned Primers 7 and 9 at a final concentration of 1 µM, 0.1 ng of the 15K gene prepared in Reference Example 4, and 2.5 units of the above-mentioned Taq polymerase was subjected to the PCR under a heat application cycle of 94° C. for 1 minute, 55° C. for 2 minutes and 72° C. for 3 minutes, with this heat application cycle being repeated 30 times, whereby a DNA fragment 18 was prepared.

(b) The DNA fragment 18 prepared in the step (a) of Example 13 was subjected to digestion at 37° C. for 1 hour with 5 units of the above-mentioned Nde I and 5 units of the above-mentioned BamH I.

The pW6A prepared in Reference Example 2 was subjected to digestion at 37° C. for 1 hour with 5 units of the above-mentioned Nde I and 5 units of the above-mentioned BamH I.

After these reactions, the DNA fragment 18 was inserted into the pW6A under the same conditions as in the step (e) in Example 1, whereby an expression vector for a 15 fused antigen was obtained. The results are shown in FIG. 6.

EXAMPLE 14
[Preparation of Expression Vector for 15-15 Fused Antigen]

(a) As a sense primer, Primer 11 prepared in Reference Example 3 was selected, and as an antisense primer, Primer 9 prepared in Example 3 was selected.

A mixture of each of the above-mentioned Primers 11 and 9 at a final concentration of 1 µM, 0.1 ng of the 15K gene prepared in Reference Example 4, and 2.5 units of the above-mentioned Taq polymerase were was subjected to the PCR under a heat application cycle of 94° C. for 1 minute, 55° C. for 2 minutes and 72° C. for 3 minutes, with this heat application cycle being repeated 30 times, whereby a DNA fragment 19 was prepared.

(b) The DNA fragment 19 prepared in the step (a) of Example 14 was subjected to digestion at 37° C. for 1 hour with 5 units of the above-mentioned Sal I and 5 units of the above-mentioned BamH I.

The expression vector for the 15-47-17 fused antigen prepared in Example 10 was subjected to digestion at 37° C. for 1 hour with 5 units of the above-mentioned Sal I and 5 units of the above-mentioned BamH I.

After these reactions, the DNA fragment 19 was inserted into an expression vector for a 15-47-17 fused antigen from which a DNA fragment 47-17 was eliminated, under the same conditions as in the step (e) in Example 1, whereby an expression vector for a 15-15 fused antigen was obtained. The results are shown in FIG. 6.

EXAMPLE 15
[Preparation of Expression Vector for 15-15-15 Fused Antigen]

(a) As a sense primer, Primer 11 prepared in Reference Example 3 was selected, and as an antisense primer, Primer 22 prepared in Example 3 was selected.

A mixture of each of the above-mentioned Primers 11 and 22 at a final concentration of 1 µM, 0.1 ng of the 15K gene prepared in Reference Example 4, and 2.5 units of the above-mentioned Taq polymerase (made by TaKaRa Co., Ltd.) was subjected to PCR under a heat application cycle of 94° C. for 1 minute, 55° C. for 2 minutes and 72° C. for 3 minutes, with this heat application cycle being repeated 30 times, whereby a DNA fragment 20 was prepared.

(b) The DNA fragment 20 prepared in the step (a) of Example 15 was subjected to digestion at 37° C. for 1 hour with 5 units of the above-mentioned Sal I and 5 units of the above-mentioned BamH I.

The expression vector for the 15-47-17 fused antigen prepared in Example 10 was also subjected to digestion at 37° C. for 1 hour with 5 units of the above-mentioned Sal I and 5 units of the above-mentioned BamH I.

After these reactions, the DNA fragment 20 was inserted into an expression vector for a 15-47-17 fused antigen from which a DNA fragment 47-17 was eliminated, under the same conditions as in the step (e) in Example 1, whereby a DNA fragment 15-15 inserted pW6A was prepared.

(c) As a sense primer, Primer 23 prepared in Reference Example 3 was selected, and as an antisense primer, Primer 24 prepared in Example 3 was selected.

A mixture of each of the above-mentioned Primers 23 and 24 at a final concentration of 1 μM, 0.1 ng of the 15K gene prepared in Reference Example 4, and 2.5 units of the above-mentioned Taq polymerase (made by TaKaRa Co., Ltd.) was subjected to PCR under a heat application cycle of 94° C. for 1 minute, 55° C. for 2 minutes and 72° C. for 3 minutes, with this heat application cycle being repeated 30 times, whereby a DNA fragment 21 was prepared.

(d) The DNA fragment 21 prepared in step (c) of Example 15 was subjected to digestion at 37° C. for 1 hour with 5 units of the above-mentioned Kpn I (made by Toyobo Co., Ltd.) and then subjected to digestion at 37° C. for 1 hour with 5 units of the above-mentioned BamH I.

The DNA fragment 15-15 inserted pW6A prepared in step (b) of Example 15 was also subjected to digestion at 37° C. for 1 hour with 5 units of the above-mentioned Kpn I (made by Toyobo Co., Ltd.) and then subjected to digestion at 37° C. for 1 hour with 5 units of the above-mentioned BamH I.

After these reactions, the DNA fragment 21 was inserted into the DNA fragment 15-15 inserted pW6A under the same conditions as in step (e) in Example 1, whereby an expression vector for a 15-15-15 fused antigen was prepared.

The results are shown in FIG. 6.

EXAMPLE 16
[Preparation of Expression Vector for 15-15-15-15 Fused Antigen]

(a) As a sense primer, Primer 23 prepared in Reference Example 3 was selected, and as an antisense primer, Primer 25 prepared in Example 3 was selected.

A mixture of each of the above-mentioned Primers 23 and 25 at a final concentration of 1 μM, 0.1 ng of the 15K gene prepared in Reference Example 4, and 2.5 units of the above-mentioned Taq polymerase (made by TaKaRa Co., Ltd.) was subjected to PCR under a heat application cycle of 94° C. for 1 minute, 55° C. for 2 minutes and 72° C. for 3 minutes, with this heat application cycle being repeated 30 times, whereby a DNA fragment 25 was prepared.

(b) The DNA fragment 22 prepared in the step (a) of Example 16 was subjected to digestion at 37° C. for 1 hour with 5 units of the above-mentioned Kpn I and then subjected to digestion at 37° C. for 1 hour with 5 units of the above-mentioned BamH I.

The DNA fragment 15-15 inserted in pW6A prepared in the step (b) of Example 15 was also subjected to digestion at 37° C. for 1 hour with 5 units of the above-mentioned Kpn I and then subjected to digestion at 37° C. for 1 hour with 5 units of the above-mentioned BamH I.

After these reactions, the DNA fragment 22 was inserted into the DNA fragment 15-15 inserted pW6A under the same conditions as in the step (e) in Example 1, whereby a DNA fragment 15-15-15 inserted pW6A was prepared. (c) As a sense primer, Primer 26 prepared in Reference Example 3 was selected, and as an antisense primer, Primer 27 prepared in Example 3 was selected.

A mixture of each of the above-mentioned Primers 26 and 27 at a final concentration of 1 μM, 0.1 ng of the 15K gene prepared in Reference Example 4, and 2.5 units of the above-mentioned Taq polymerase (made by TaKaRa Co., Ltd.) was subjected to PCR under a heat application cycle of 94° C. for 1 minute, 55° C. for 2 minutes and 72° C. for 3 minutes, with this heat application cycle being repeated 30 times, whereby a DNA fragment 23 was prepared.

(d) The DNA fragment 23 prepared in the step (c) of Example 16 was subjected to digestion at 37° C. for 1 hour with 5 units of the above-mentioned Kpn I and then subjected to digestion at 37° C. for 1 hour with 5 units of the above-mentioned Hind III (made by Toyobo Co. Ltd.).

The DNA fragment 15-15-15 inserted pW6A prepared in the step (b) of Example 16 was also subjected to digestion at 37° C. for 1 hour with 5 units of the above-mentioned Kpn I and then subjected to digestion at 37° C. for 1 hour with 5 units of the above-mentioned Hind III (made by Toyobo Co. Ltd.).

After these reactions, the DNA fragment 23 was inserted into the DNA fragment 15-15-15 inserted pW6A under the same conditions as in the step (e) in Example 1, whereby an expression vector for a 15-15-15-15 fused antigen was prepared.

The results are shown in FIG. 6.

EXAMPLE 17
[Expression of Each Fused Antigen]

*Escherichia coli* BL21 (DE3), which is a competent cell prepared by Hanahan method, was transformed using each of the above-mentioned expression vectors obtained in Examples 1 to 12.

The transformation culture thereof was then plated on an LB agar plate containing 50 μg/ml of ampicillin and incubated at 37° C. overnight. From the mixture of ampicillin-resistant *Escherichia coli* cells thus produced, there was selected the transformant carrying an expression vector for each fused antigen in which each fused antigen gene was integrated.

Each of the thus selected transformant was then inoculated to 4 ml of an LB liquid medium containing 50 μg/ml of ampicillin, and cultured with shaking at 37° C. overnight.

The thus obtained culture was further inoculated into 1 l of an LB liquid culture medium containing 50 μg/ml of ampicillin, and cultured with shaking at 37° C. for 3 hours.

To the thus cultured *Escherichia coli*, IPTG (isopropyl-β-D(-)-thiogalactopyranoside) was added at a final concentration of 1 mM.

Cultivation was then further continued with shaking at 37° C. overnight, whereby the expression of each fused antigen was carried out.

EXAMPLE 18
[Purification of Fused Antigens]

47-17-15 fused antigen, 47-15-17 fused antigen, 15-17-47 fused antigen, and 15-17 fused antigen were purified.

The fused antigens of a three-antigen-fused type, namely, 47-17-15 fused antigen, 47-15-17 fused antigen, and 15-17-47 fused antigen were purified by the steps of subjecting each antigen-expressed *Escherichia coli* to ultrasonic blending and centrifugation, followed by making the residue soluble, using urea, and subjecting the antigen to gel filtration chromatography using Superdex-200 (Pharmacia Biotec Co., Ltd.), ion-exchange chromatography using Q-Sepharose (Pharmacia Biotec Co., Ltd.), and absorption chromatography using ceramic hydroxyapatite (made by Asahi Optical Co., Ltd.).

The fused antigen of a two-antigen-fused type, namely, 15-17 fused antigen was purified by the steps of subjecting the antigen-expressed *Escherichia coli* to ultrasonic blending and centrifugation, pooling the supernatant, adding urea thereto, and subjecting the antigen to ion-exchange chromatography using Q-Sepharose (made by Pharmacia Biotec Co., Ltd.), absorption chromatography using ceramic hydroxyapatite (made by Asahi Optical Co., Ltd.), and then ion-exchange chromatography using SP-Sepharose (made by Pharmacia Biotec Co., Ltd.).

7 mg of 47-17-15 fused antigen, 10 mg of 47-15-17 fused antigen, 20 mg of 15-17-47 fused antigen and 10 mg of 15-17 fused antigen were obtained with a purity of 95% or more from one litter of the respective culture media.

Figure 7:
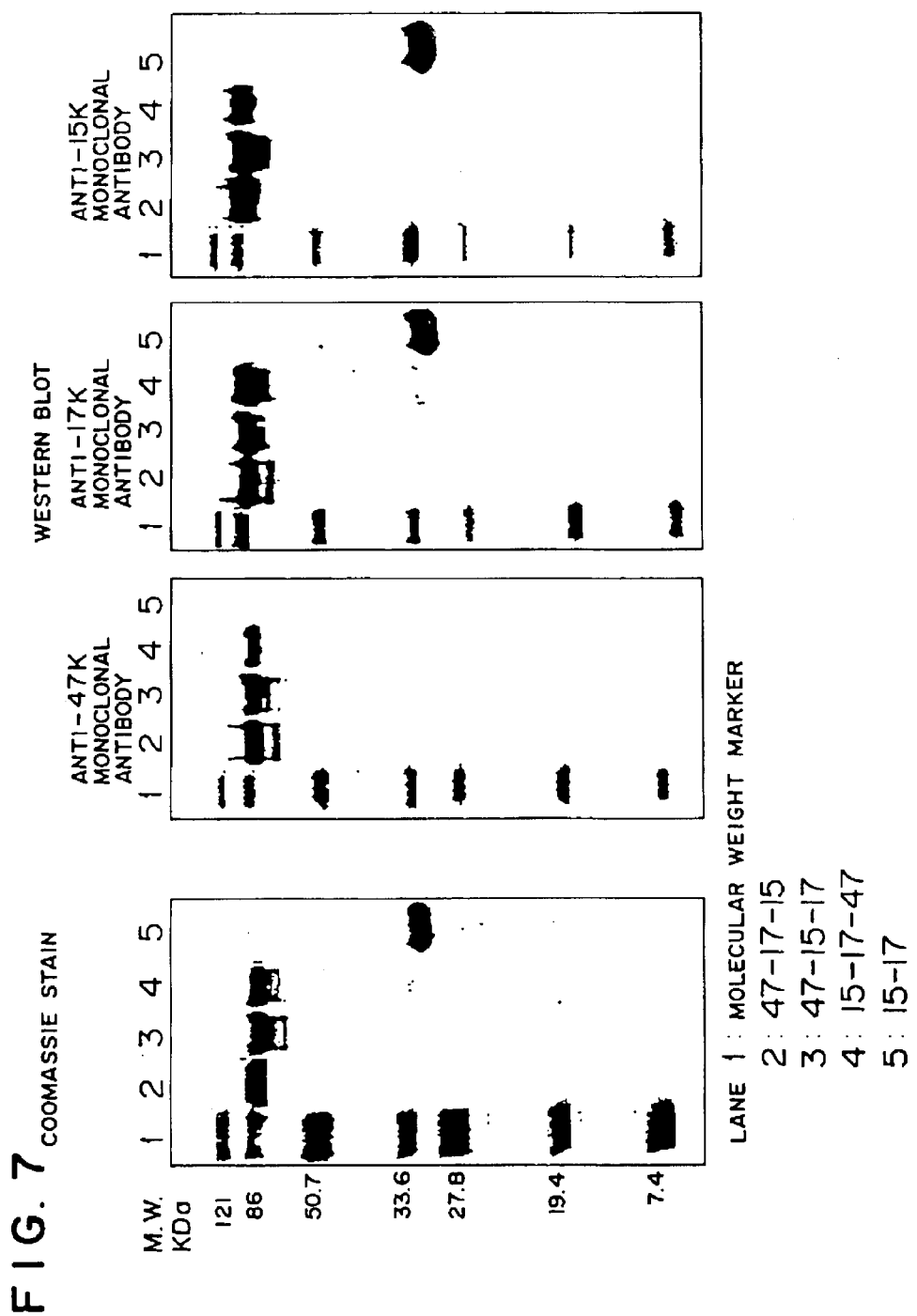
FIG. 7 are electrophoresis diagrams of purified fused antigens.

After the purification, each fused antigen was subjected to reduction SDS-polyacrylamide gel electrophoresis and then to coomassie staining. The results are shown in FIG. 7.

It was expected that the antigens of the three-antigen-fused type had a molecular weight of 75K and that 15-17 fused antigen had a molecular weight of 29K in view of the respective amino acid sequences thereof. It was confirmed that the above expectation was correct by the electrophoretic analyses thereof.

By Western blotting which was conducted by use of 47KMab, 17KMab and 15KMab which were prepared in Reference Example 1, it was confirmed that these monoclonal antibodies were reactive with the corresponding antigens in each of the fused antigens.

EXAMPLE 19
[Preparation of Fused Antigen Bound Plate]

Each of the fused antigens purified in Example 18 was diluted with 10 mM PBS, placed in an amount of 0.66 pmol/well in each well of a 96-well ELISA plate (made by Becton Dickinson Co., Ltd.) and allowed to stand at 4° C. overnight, whereby the fused antigen was bound to each well. After this binding, each fused antigen bound well was blocked with 10 mM PBS containing 1% skim milk at 37° C. for 2 hours.

REFERENCE EXAMPLE 5
[Preparation of Single Antigen Bound Plate]

Each of a recombinant single antigen 47K antigen expressed by *Escherichia coli* and purified, a 17K antigen including a signal peptide at the N-terminus thereof (hereinafter referred to as S17K antigen), and GST15K antigen was bound in an amount of 0.66 pmol/wel to a well.

Furthermore, a mixture of the above-mentioned recombinant single antigen 47K antigen, S17K antigen, and GST15K antigen was bound in an amount of 0.66 pmol/wel to a well.

After the above-mentioned binding, the wells were blocked with 10 mM PBS containing 1% skim milk at 37° C. for 2 hours.

EXAMPLE 20
[Tests for Reactivity between Fused Antigens and Monoclonal Antibodies]

Each of 47KMab, 17KMab, 15KMab and a mixture thereof was diluted with 10 mM PBS containing 1% of skim milk and 0.05% Tween 20 (Trademark) (hereinafter referred to as the skim milk containing PBST) to such a dilution degree that the final concentration of each monoclonal antigen was 10 $\mu$m/ml.

Each of the above diluted monoclonal antigen and the above-mentioned mixture was added in an amount of 50 $\mu$l to each of the washed wells of the antigen-bound plates prepared in Example 19 and Reference Example 5, and was then incubated at room temperature for 1 hour and 30 minutes.

After each of the wells was washed, 50 $\mu$l of a peroxidase labeled anti-mouse Ig (made by DAKO Co., Ltd.) diluted to $\frac{1}{1000}$ with the skim milk containing PBST was added to each well, and the mixture was incubated at room temperature for 1 hour and 30 minutes.

After each of the wells was washed, 50 $\mu$l of a mixed solution of a hydrogen peroxide solution and ABTS was added thereto, and ABTS was colored for 3 minutes. After the termination of the reaction, the absorbance thereof with 405 nm thereof was measured by a spectrophotometer.

The results are shown in TABLE 1. As shown in TABLE 1, the fused antigens exhibit the same activity as or higher activity than that of any of the single antigens, 47K, S17K and GST15K.

TABLE 1

|  |  | 47KMab | 17KMab | 15KMab | 47KMab + 17KMab + 15KMab |
|---|---|---|---|---|---|
| Fused Antigens | 47-17-15 | 0.56 | 0.35 | 0.47 | 1.48 |
|  | 47-15-17 | 1.26 | 0.51 | 0.52 | 1.53 |
|  | 15-17-47 | 1.21 | 0.76 | 1.26 | 1.89 |
|  | 15-17 | — | 0.13 | 0.60 | 0.36 |
| Single Antigens | 47K | 0.52 | — | — | — |
|  | S17K | — | 0.05 | — | — |
|  | GST15K | — | — | 0.45 | — |
|  | 47K + S17K + GST15K | — | — | — | 0.95 |

EXAMPLE 21
[Comparative Tests Concerning Reactivities between Fused Antigens and Single Antigens]

50 $\mu$l of each of a Tp positive serum (purchased from Boston Biomedica Inc.) which was diluted to $\frac{1}{1000}$ with the skim milk containing PBST, and a Tp negative serum was added to each well of the washed antigen bound plates which were prepared in Example 19 and Reference Example 5

Each of the above-mentioned serums was incubated at room temperature for 1 hour and 30 minutes.

After each of the wells was washed, 50 $\mu$l of a peroxidase labeled antihuman Ig G (made by BIO SOURCE Co., Ltd.) diluted to $\frac{1}{1000}$ with the skim milk containing PBST was added to each well, and the mixture was incubated at room temperature for 1 hour and 30 minutes.

After each of the wells was washed, 50 $\mu$l of a mixed solution of a hydrogen peroxide solution and ABTS was added thereto, and ABTS was colored for 3 minutes. After the termination of the reaction, the absorbance thereof with 405 nm thereof was measured by a spectrophotometer.

The results are shown in TABLE 2. As shown in TABLE 2, the fused antigens exhibit higher reactivity with the positive serum than the single antigens and the mixture thereof, and never react with the negative serum.

TABLE 2

|  |  | Positive Serum | Negative Serum |
|---|---|---|---|
| Fused Antigens | 47-17-15 | 0.56 | 0.02 |
|  | 47-15-17 | 1.18 | 0.02 |
|  | 15-17-47 | 1.13 | 0.03 |
|  | 15-17 | 0.44 | 0.01 |
| Single Antigens | 47K | 0.13 | 0.03 |
|  | S17K | 0.11 | 0.01 |
|  | GST15K | 0.16 | 0.02 |
|  | 47K + S17K + GST15K | 0.39 | 0.03 |

EXAMPLE 22
[Reactivity Tests between Fused Antigens and Positive Serum]

24 examples of Tp positive serums (purchased from Boston Biomedica Inc.) and one example of Tp negative serum were tested in the same manner as in Example 21 except that the coloring time was extended to 30 minutes.

The results are shown in TABLE 3. The reactivities of the fused antigens with 24 examples of the positive serums were significantly higher than that of the fused antigens with the negative serum.

TABLE 3

| | | Solid Phase Antigens | | | |
|---|---|---|---|---|---|
| | | 47-17-15 | 47-15-17 | 15-17-47 | 15-17 |
| Positive Serums | No. 1 | 0.54 | 1.15 | 1.85 | 0.81 |
| | No. 2 | >2 | >2 | >2 | 1.47 |
| | No. 3 | 1.51 | >2 | >2 | 1.72 |
| | No. 4 | >2 | >2 | >2 | >2 |
| | No. 5 | 0.52 | 1.29 | 1.57 | 0.95 |
| | No. 6 | 0.34 | 0.64 | 1.08 | 0.35 |
| | No. 7 | >2 | >2 | >2 | >2 |
| | No. 8 | >2 | >2 | >2 | >2 |
| | No. 9 | 0.56 | 1.05 | 1.40 | 0.69 |
| | No. 10 | >2 | >2 | >2 | >2 |
| | No. 11 | >2 | >2 | >2 | >2 |
| | No. 12 | 1.30 | >2 | >2 | 1.21 |
| | No. 13 | 1.79 | >2 | >2 | 1.55 |
| | No. 14 | >2 | >2 | >2 | >2 |
| | No. 15 | >2 | >2 | >2 | >2 |
| | No. 16 | >2 | >2 | >2 | >2 |
| | No. 17 | 1.39 | >2 | >2 | 1.25 |
| | No. 18 | >2 | >2 | >2 | >2 |
| | No. 19 | 1.62 | >2 | >2 | 1.29 |
| | No. 20 | 0.64 | 1.08 | 1.28 | 0.73 |
| | No. 21 | >2 | >2 | >2 | >2 |
| | No. 22 | 0.42 | 1.11 | 1.41 | 0.77 |
| | No. 23 | 0.57 | 1.52 | 1.43 | 0.91 |
| | No. 24 | >2 | >2 | >2 | >2 |
| Negative Serum | | 0.06 | 0.08 | 0.07 | 0.06 |

EXAMPLE 23

[Expression of 15K, 15K-15K, 15K-15K-15K and 15K-15K-15K-15K]

*Escherichia coli* BL21 (DE3) was transformed using each of the 15K, 15K-15K, 15K-15K-15K and 15K-15K-15K-15K expression vectors obtained in Examples 13 to 16.

The transformation culture thereof was then plated on an LB agar plate containing 50 μg/ml of ampicillin and incubated at 37° C. overnight. From the mixture of ampicillin-resistant *Escherichia coli* cells thus produced, the transformant was selected carrying an expression vector for each fused antigen in which each fused antigen gene was integrated.

Each of the thus selected transformants was inoculated to 2 ml of an LB liquid medium containing 50 μg/ml of ampicillin, and cultured with shaking at 37° C. overnight.

40 μl of the thus obtained culture was inoculated to 2 ml of an LB liquid medium containing 50 μg/ml of ampicillin and further cultured with shaking at 37° C. for 2 hours. To the thus cultured *Escherichia coli*, IPTG (isopropyl-β-D(–)-thiogalactopyranoside) was added at a final concentration of 1 mM.

Cultivation was then further continued with shaking at 37° C. overnight, whereby the expression of each fused antigen was carried out.

Out of 2 ml of the thus obtained culture, 1.5 ml thereof was transferred into a micro centrifugation tube and centrifuged at 15000 rpm for 30 seconds by use of a micro centrifuge (Trademark "himac CT 15D" made by Hitachi Ltd.), whereby a cell pellet of the desired *Escherichia coli* transformant was collected.

Each cell pellet was resuspended in 150 μl of TE Buffer (10 mM tris-hydrochloric acid buffer, pH 8.0, 0.1 mM, EDTA), and 150 μl of x2 sample buffer (1M tris-hydrochloric acid buffer, pH 6.8, 20%w/v SDS, 10%v/v β-ME), and boiled for 5 minutes. Then, each sample was subjected to ultrasonic treatment for 10 minutes.

To 13 μl of the thus obtained sample, 2 μl of 50% glycerin was added, and the mixture was mixed. 10 μl of the mixture was then electrophoresed on the 15% SDS-polyacrylamide gel under the reducing condition (Laemmli, U.K. 1970: Nature 227, 680), and was coomassie blue R stained.

Figure 8:
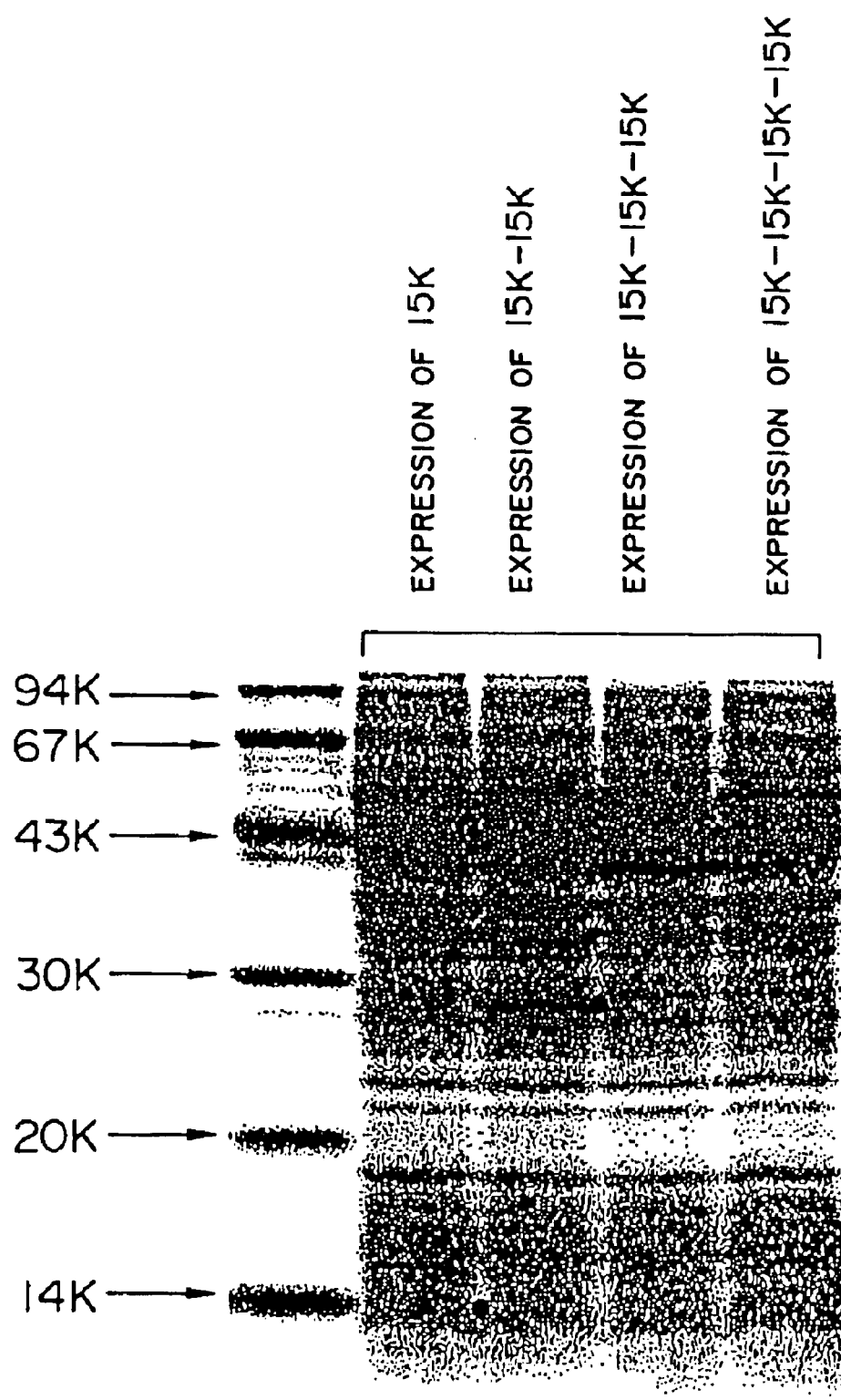
FIG. 8 is an electrophoresis diagram of a fused antigen in which 15K is repeatedly fused.

The results are shown in FIG. 8.

By the overnight expression, the presence of 15K-15K, 15K-15K-15K and 15K-15K-15K-15K bands was confirmed.

Furthermore, each antigen expressed overnight was also subjected to SDS-PAGE in the same manner as mentioned above on the 10 to 15% polyacrylic amide gradient gel, and then subjected to western blotting with the 15KMab prepared in Reference Example 1.

Figure 9:
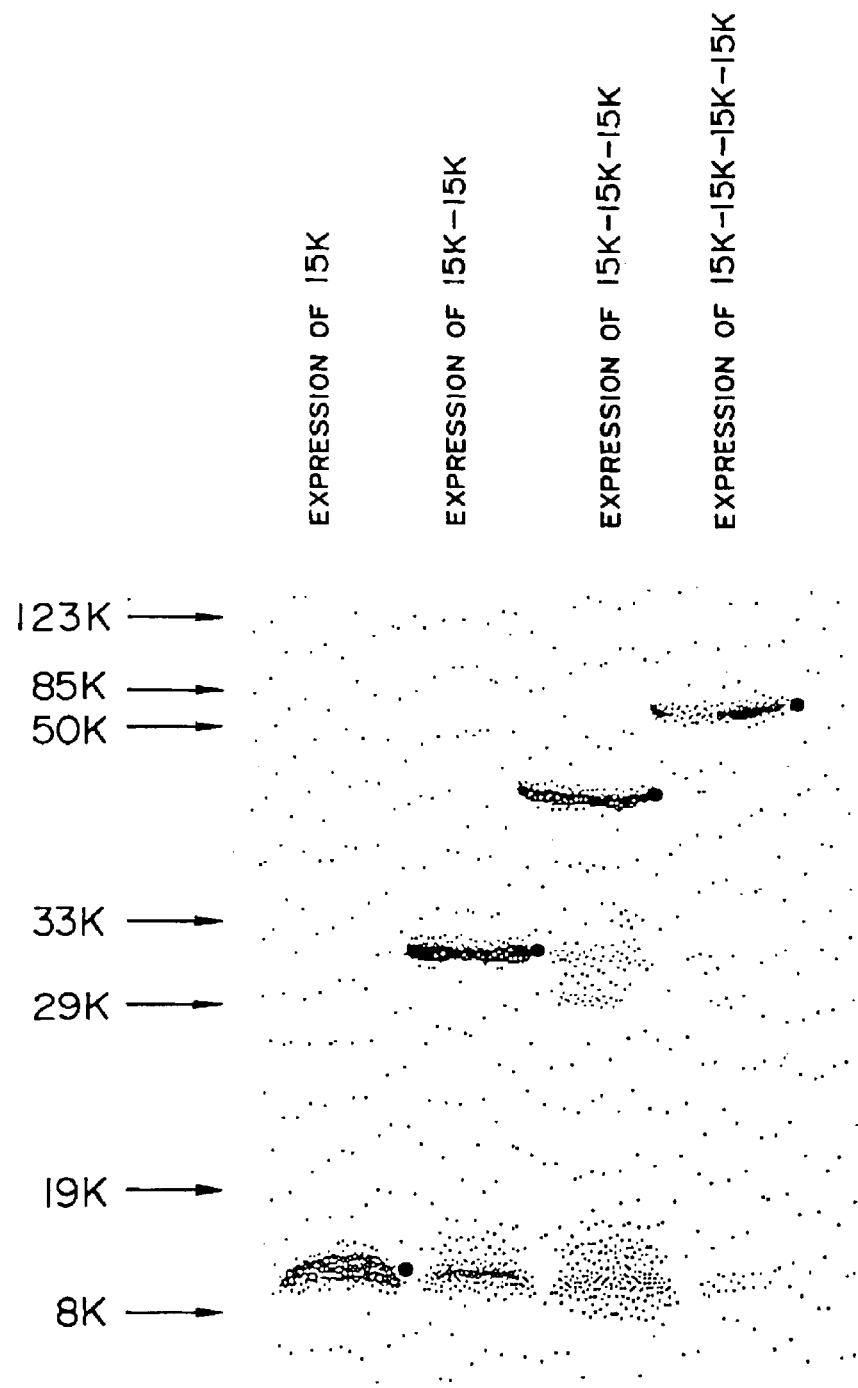
FIG. 9 is a Western Blotting diagram of a fused antigen in which an expressed 15K is repeatedly fused.

The result was that as shown in FIG. 9, the presence of all of the 15K, 15K-15K, 15K-15K-15K and 15K-15K-15K-15K bands was confirmed.

EXAMPLE 24

[Comparison among Expression Amounts of 15K, 15K-15K, 15K-15K-15K and 15K-15K-15K-15K]

An electrophoresis sample which was prepared as shown in Example 23, and molecular mass standards containing a known concentration of BSA (Trademark "Low Molecular Weight Calibration Kit" made by Pharmacia LKB) were electrophoresed on the 15% SDS-polyacrylamide gel under reducing conditions, and were coomassie blue R stained. The results are shown in FIG. 10.

The amounts of the expressed antigens were calculated from the stained bands thereof by use of a densitometer (Trademark "Densitograph AE-6900" made by Atto Co., Ltd.)

Figure 10:
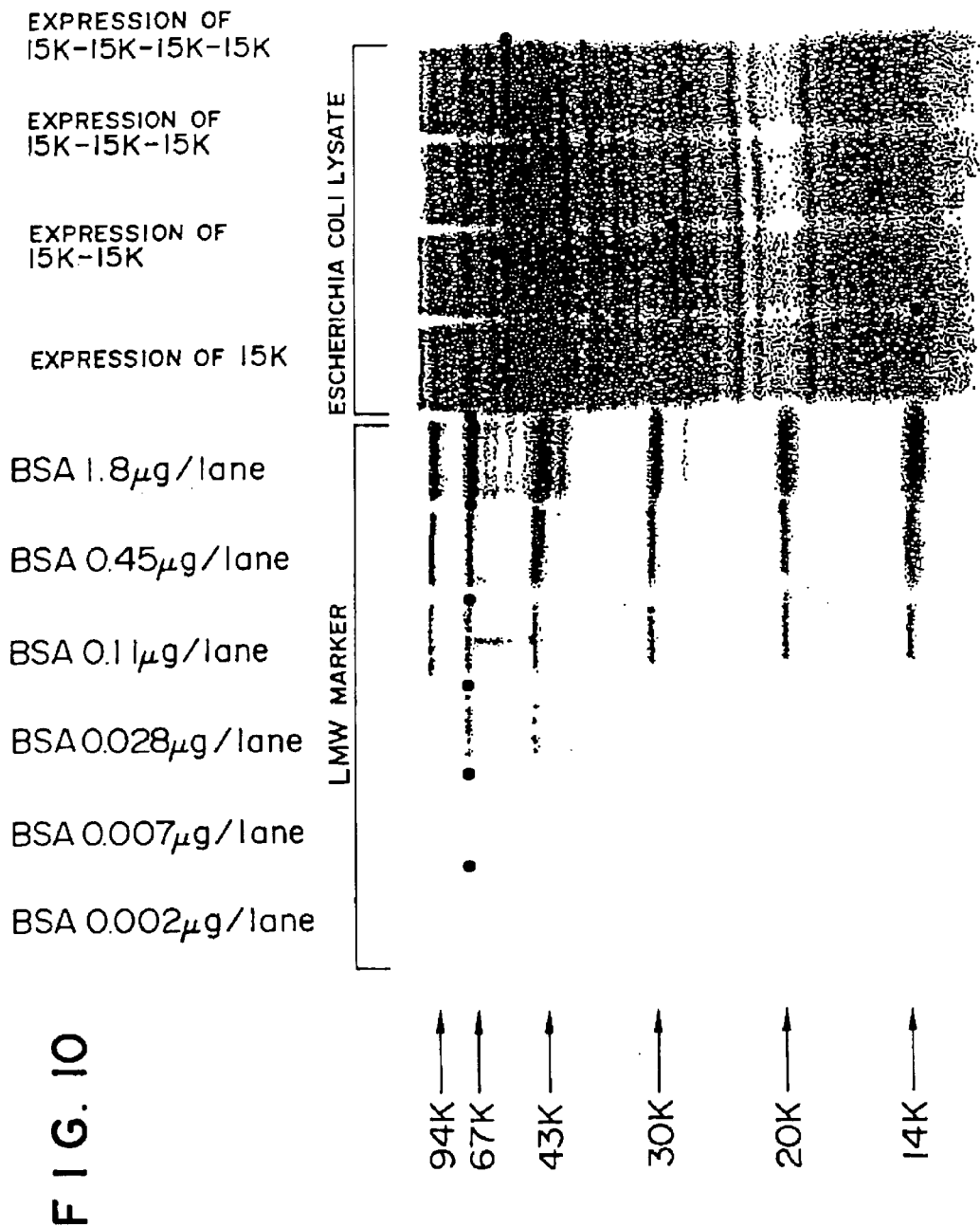
FIG. 10 is a diagram of an electrophoresis for quantitative measurement of a fused antigen in which 15K was repeatedly fused.
Figure 11:
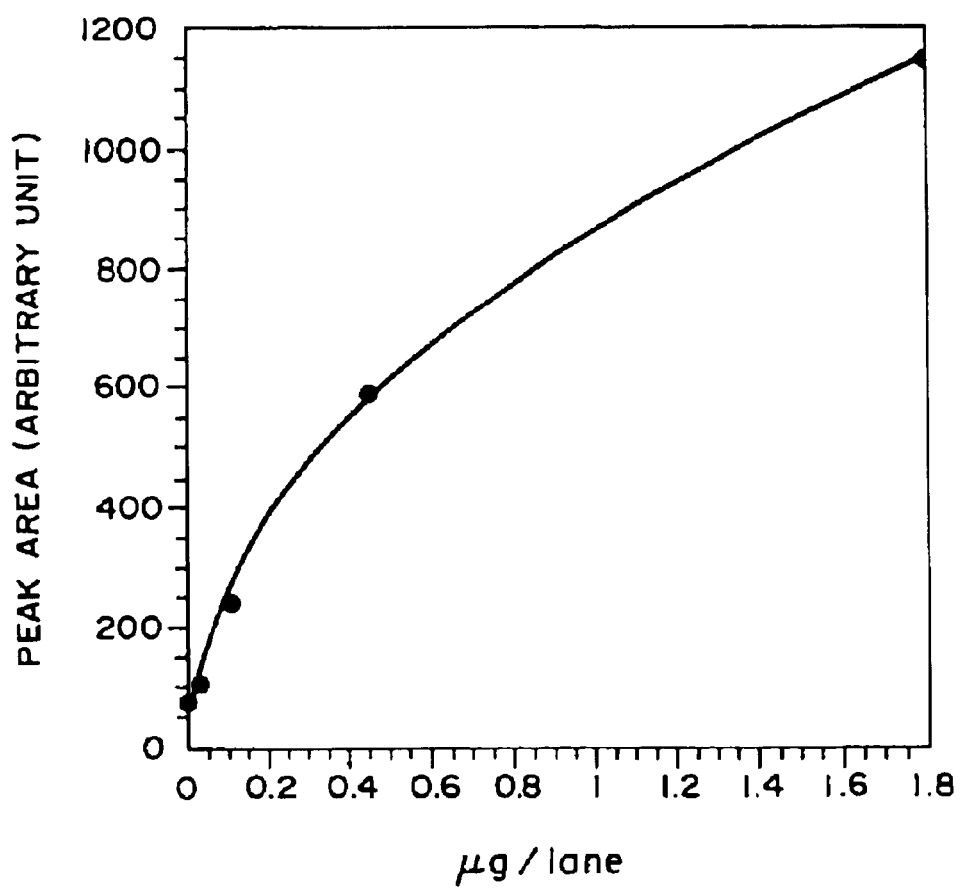
FIG. 11 is a graph showing a working curve for the quantitative measurement of a band on an electrophoresed gel prepared by use of BSA.

From the coomassie blue R stained gel in FIG. 10, the density of the bands of BSA with a known concentration was measured by the densitometer, whereby a working curve as shown in FIG. 11 was obtained. Furthermore, the densities of the bands corresponding to the 15K, 15K-15K, 15K-15K-15K and 15K-15K-15K-15K were also measured in the same manner as mentioned above by use of the densitometer, and the respective expression amounts were calculated by use of the working curve shown in FIG. 11. The results are shown in TABLE 4 as shown below.

TABLE 4

| Kinds of Antigens | Peak Area (Arbitrary Unit) | Concentration of Protein (μg/lane) |
|---|---|---|
| 15K | n.d | n.d |
| 15K-15K | 499 | 0.34 |
| 15K-15K-15K | 856 | 1.0 |
| 15K-15K-15K-15K | 436 | 0.27 |

With respect to the 15K, no bands were observed. In contrast to this, with respect to the 15K-15K-15K, the expression amount thereof was 1 μg per lane (corresponding to 23 mg per 1 litter of the culture), which was the largest of all the tested samples. By fusing 15K repeatedly in this manner, the expression amount thereof was significantly increased.

Japanese Patent Application No. 7-350072 filed Dec. 25, 1995 is hereby incorporated by reference.

What is claimed is:

1. An assay method for detecting anti-*Treponema pallidum* antibodies in a sample, comprising:

reacting with said sample a *Treponema pallidum* fused antigen, wherein the fused antigen consists of a plurality of surface antigens of *Treponema pallidum*, wherein said surface antigens include at least one antigen selected from the group consisting of 15-kilodalton surface antigen of *Treponema pallidum,* 17-kilodalton surface antigen of *Treponema pallidum*, and 47-kilodalton surface antigen of *Treponema pallidum*; and detecting the reaction of said fused antigen with said antibodies.

2. The method of claim 1, wherein the fused antigen consists of two amino acid sequences, each constituting a surface antigen of *Treponema pallidum* selected from the group consisting of the 15-kilodalton surface antigen and the 17-kilodalton surface antigen, wherein the 15-kilodalton antigen is amino terminal to the 17-kilodalton antigen, or the 17-kilodalton antigen is amino terminal to the 15-kilodalton antigen.

3. The method of claim 1, wherein the fused antigen consists of two amino acid sequences, each constituting a surface antigen of *Treponema pallidum* selected from the group consisting of the 15-kilodalton and the 47-kilodalton antigen, wherein a 15-kilodalton antigen is amino terminal to the 47-kilodalton antigen, or the 47-kilodalton antigen is amino terminal to the 15-kilodalton antigen.

4. The method of claim 1, wherein the fused antigen consists of two amino acid sequences, each constituting a surface antigen of *Treponema pallidum* selected from the group consisting of the 17-kilodalton and the 47-kilodalton antigen, wherein a 17-kilodalton antigen is amino terminal to the 47-kilodalton antigen, or the 47-kilodalton antigen is amino terminal to the 17-kilodalton antigen.

5. The method of claim 1, wherein the fused antigen consists of two amino acid sequences, each constituting the 15-kilodalton antigen.

6. The method of claim 1, wherein the fused antigen consists of three amino acid sequences which are 15-kilodalton surface antigen of *Treponema pallidum,* 17-kilodalton surface antigen of *Treponema pallidum*, and 47-kilodalton surface antigen of *Treponema pallidum*.

7. The method of claim 1, wherein the fused antigen consists of four amino acid sequences which may be the same or different, each constituting a surface antigen of *Treponema pallidum* selected from the group consisting of the 15-kilodalton antigen, the 17-kilodalton antigen, and the 47-kilodalton antigen.

8. The method of claim 1, wherein the fused antigen includes at least two surface antigens selected from the group consisting of 15-kilodalton surface antigen of *Treponema pallidum*, and 47-kilodalton surface antigen of *Treponema pallidum*, said at least two surface antigens of *Treponema pallidum* being the same or different.

9. The method of claim 1, wherein said fused antigen is bound to a carrier.

10. The method of claim 9, wherein said carrier is selected from the group consisting of latex particles, gelatin particles, and magnetic particles.

11. The method of claim 1, further comprising measuring the amount of said antibodies in said sample.

12. The method of claim 1, wherein said detecting is accomplished by agglutination.

13. The method of claim 1, wherein the reaction of said fused antigen with said antibodies is detected with an antihuman immunoglobin labeled with an enzyme.

14. The method of claim 13, wherein said enzyme is peroxidase.

* * * * *

SEQUENCE LISTING

<160> NUMBER OF SEQ ID NOS: 30

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 1
tagcccatat gggctcgtct catcatgag                                         29

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 2
atagaactaa atgaacaaga cacacgggat aggacac                                37

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
tgttcattta gttctatccc                                                   20

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
tgtgcacgag acacacctgc taataatggc ttcct                                  35

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
tgtgtctcgt gcacaaccgt                                                   20

<210> SEQ ID NO 6
<211> LENGTH: 35
<212> TYPE: DNA
<213> ORGANISM: Artificial Sequence
<220> FEATURE:

<223> OTHER INFORMATION: Description of Artificial Sequence:Synthetic
      DNA

<400> SEQUENCE: 6
gatccggatc cctatttctt tgttttttg agcac                          35

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
tagcccatat gtgttcattt agttctatc                                29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
tagcccatat gtgtgtctcg tgcacaacc                                29

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
gatccggatc cctacctgct aataatggct t                             31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
gatccggatc cctaagacac acgggatagg a                             31

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
cgaggcgtcg actgttcatt tagttctatc                               30

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:Synthetic

DNA

<400> SEQUENCE: 12
gaacgtcgac tgtggctcgt ctcatcat                                28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 13
cttgctcgag agacacacgg gataggac                                28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 14
agtagtcgac tgtgtctcgt gcacaacc                                28

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 15
cagactcgag tttctttgtt tttttgagca c                            31

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 16
cagagtcgac tttctttgtt tttttgagca c                            31

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 17
gctagtcgac cctgctaata atggcttc                                28

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

```
<400> SEQUENCE: 18
cgtagagctc agacacacgg gataggacac                                    30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 19
tagcgagctc tgtgtctcgt gcacaaccgt                                    30

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 20
gatccggatc cctaagacac acgggatagg acacccctct tctgggccac taccttcgc    59

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 21
ctcttgtcga cagacacacg ggataggac                                     29

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 22
ccggggatcc cctgctaata atggcttc                                      28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 23
ccggggatcc tgttcattta gttctatc                                      28

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA
```

```
<400> SEQUENCE: 24
ccggggtacc ctacctgcta ataatggctt c                           31

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 25
ccggggtacc cctgctaata atggcttc                               28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 26
ccggggtacc tgttcattta gttctatc                               28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 27
ccggaagctt ctacctgcta ataatggc                               28

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 28
gactgaattc tttctttgtt tttttgagca c                           31

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 29
ggtggaattc tgttcattta gttctatccc g                           31

<210> SEQ ID NO 30
<211> LENGTH: 9
<212> TYPE: PRT
<213> ORGANISM: Treponema pallidum
```

```
<400> SEQUENCE: 30

Lys Arg Gly Val Leu Ser Arg Val Ser
 1               5
```